United States Patent
Vic et al.

(10) Patent No.: US 9,498,426 B2
(45) Date of Patent: Nov. 22, 2016

(54) PROCESS FOR TREATING HAIR FIBERS USING POLYSILOXANE/POLYUREA

(75) Inventors: Gabin Vic, Semoy (FR); Gaëlle Brun, Paris (FR); Luc Gourlaouen, Asnieres (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/440,984

(22) Filed: Apr. 5, 2012

(65) Prior Publication Data

US 2012/0192887 A1    Aug. 2, 2012

Related U.S. Application Data

(63) Continuation of application No. 12/334,765, filed on Dec. 15, 2008, now abandoned.

(60) Provisional application No. 61/009,210, filed on Dec. 27, 2007.

(30) Foreign Application Priority Data

Dec. 13, 2007 (FR) ...................................... 07 59812

(51) Int. Cl.
   *A61K 8/898*     (2006.01)
   *A61Q 5/06*      (2006.01)

(52) U.S. Cl.
   CPC ................. *A61K 8/898* (2013.01); *A61Q 5/06* (2013.01)

(58) Field of Classification Search
   None
   See application file for complete search history.

(56) References Cited

U.S. PATENT DOCUMENTS

| 5,643,581 | A  | * | 7/1997  | Mougin et al. ............... 424/401 |
| 6,166,093 | A  | * | 12/2000 | Mougin .................. A61K 8/87 424/401 |
| 6,319,959 | B1 | * | 11/2001 | Mougin et al. ............ 514/772.1 |
| 6,395,265 | B1 | * | 5/2002  | Mougin et al. ............ 424/70.12 |
| 6,626,962 | B1 |   | 9/2003  | Lang et al. |
| 7,976,831 | B2 | * | 7/2011  | Fondin et al. ............. 424/70.51 |
| 8,337,822 | B2 | * | 12/2012 | Brun ......................... 424/70.12 |
| 2005/0031566 | A1 | * | 2/2005 | Cooper et al. ............. 424/70.11 |
| 2005/0125914 | A1 | * | 6/2005 | Malle et al. ..................... 8/406 |
| 2005/0137327 | A1 | * | 6/2005 | Ziche ............................ 524/838 |
| 2005/0232882 | A1 |   | 10/2005 | Bebot et al. |
| 2008/0127429 | A1 |   | 6/2008  | Brun et al. |
| 2008/0171010 | A1 | * | 7/2008  | Brun ....................... A61Q 5/12 424/70.12 |

FOREIGN PATENT DOCUMENTS

| EP | 1 582 198 | 10/2005 |
| FR | 2 743 297 | 7/1997 |
| WO | WO 2005/087186 | 9/2005 |

* cited by examiner

*Primary Examiner* — Susan Tran
(74) *Attorney, Agent, or Firm* — The Marbury Law Group, PLLC

(57) ABSTRACT

A process for treating hair fibers comprising: applying to the hair fibers at least one cosmetic composition comprising, in a cosmetically acceptable medium, at least one polysiloxane/polyurea block copolymer; and subsequently or simultaneously heating the hair fibers at a temperature ranging from 50 to 280° C.

12 Claims, No Drawings

PROCESS FOR TREATING HAIR FIBERS USING POLYSILOXANE/POLYUREA

This application claims benefit of U.S. Provisional Application No. 61/009,210, filed Dec. 27, 2007, the contents of which are incorporated herein by reference. This application also claims benefit of priority under 35 U.S.C. §119 to French Patent Application No. FR 0 759 812, filed Dec. 13, 2007, the contents of which are also incorporated herein by reference. This application is a continuation of U.S. patent application Ser. No. 12/334,765, filed Dec. 15, 2008, now abandoned which is incorporated herein by reference.

Disclosed herein is a process for treating hair fibers using at least one specific polymer.

There are many styling products that can make it possible to shape hair. For example, styling gels or mousses can make it possible to structure a head of hair in the form of locks or more sophisticated forms, such as curls or waves, when a suitable heating device is used. However, the locks obtained with these products can be very stiff, and can lack sheen and shape-retention over time. That is to say that over the course of a day the shape of these locks may rapidly disappear.

Another important problem that can be linked to the use of gels and mousses with an iron-type heating device is the fact that the shape given to the lock of hair may be difficult to change subsequently. The hair shaping properties of the product are frequently lost when heat is reapplied. Deposits are also frequently formed on the heating devices, which can necessitate regular cleaning of the equipment.

Furthermore, other hair-treatment processes involve heating the hair. However, heating the hair can have a damaging effect on the fibers.

Many hair-treatment processes use silicone compounds. This is because it is known that silicone compounds are cosmetic active agents that can improve the cosmetic properties of the hair. They can also have a conditioning effect on the hair and provide sheen.

However, the sheen provided by silicones frequently have a tendency to fade rapidly with time.

Accordingly, there is a need in the art for a process for treating hair fibers that can make it possible to easily shape the hair and to give it a desired relief. This resultant hair shaping should be thermoreversible, that is to say that a new shape may be given to the lock of hair when it is subjected to heat again, without an additional supply of formula. It is also desired to obtain a very high sheen and a very good feel in a long-lasting manner for the hair fibers.

European Patent Application 1,582,198 discloses a process for treating hair fibers that comprises the following steps:

applying a composition comprising at least 5% by weight, relative to the total weight of the composition, of at least one silicone chosen from aryl silicones and silicone gums to the hair fibers; then raising the temperature of the hair fibers, using a heated flat iron, to a temperature ranging from 150 to 250° C.

The results obtained with this process do not always make it possible, however, to obtain the desired effects for example in terms of hair shaping.

The present inventors have found, surprisingly, that it is possible to overcome at least one of the drawbacks of the prior art and to meet at least one the aforementioned objectives, Disclosed herein is a process for treating hair fibers comprising:

applying at least one cosmetic composition comprising, in a cosmetically acceptable medium, at least one polysiloxane/polyurea block copolymer to the hair fibers; and simultaneously or successively heating the hair fibers at a temperature ranging from 50 to 280° C.

In the present disclosure the application of such a composition to the hair can be easy. It can form, after heat treatment, a homogeneous lock (group of united hairs). The polymer deposit formed on the hair can be homogeneous, smooth and can have excellent adhesion. The cosmetic feel of the coated hair and its softness can be very good. The sheen can also very good.

The properties obtained can be durable, that is to say they may not require reapplication of product to last over time.

This hair shaping can be thermoreversible, that is to say that a new shape may be given to the lock of hair when it is subjected to heat again, without an additional supply of the cosmetic composition.

Polysiloxane/Polyurea Block Copolymer

As used herein, the term "block copolymer" means a copolymer comprising at least two separate sequences of each of the polymers constituting the copolymer in the backbone of the copolymer. For example, the copolymer of the present disclosure comprises at least one polysiloxane sequence (or block) and at least one polyurea sequence (block) in the backbone of the copolymer.

The copolymer of the present disclosure may comprise, in addition to the polysiloxane/polyurea, other blocks of different units, including but not limited to polysiloxane/polyurea/polyurethane block terpolymers.

In at least one embodiment, the copolymer comprises an amount, by weight, of polysiloxane greater than 5%. In at least one embodiment, the amount of polysiloxane present in the copolymer is greater than 90% by weight relative to the total weight of the copolymer.

According to one aspect of the present disclosure, the copolymer comprises only at least one siloxane block and at least one polyurea block.

According to the present disclosure, the at least one copolymer can be chosen from those of formula (I):

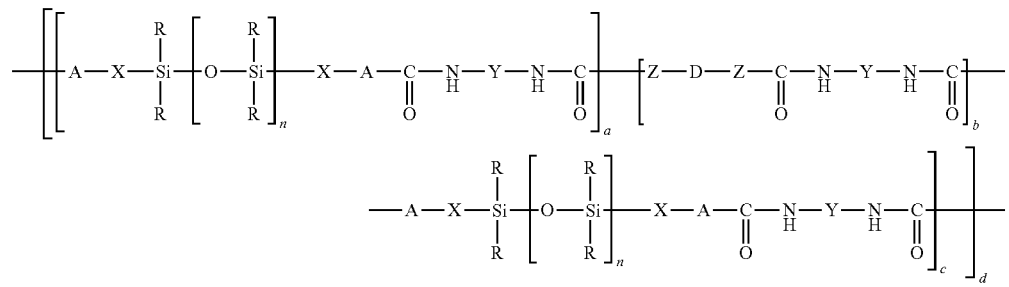

wherein:

R is a monovalent hydrocarbon-based radical, optionally substituted by fluorine or chlorine, having 1 to 20 carbon atoms;

X is an alkylene radical having 1 to 20 carbon atoms, wherein non-neighboring methylene units may be replaced by —O— radicals;

A is an oxygen atom or an —NR'— amino radical;

Z is an oxygen atom or an —NR'— amino radical;

R' is hydrogen or an alkyl radical having 1 to 10 carbon atoms;

Y is a divalent hydrocarbon-based radical, optionally substituted by fluorine or chlorine, having 1 to 20 carbon atoms;

D is an alkylene radical, optionally substituted by fluorine, chlorine, $C_1$-$C_6$ alkyl or $C_1$-$C_6$ alkyl ester, having 1 to 700 carbon atoms, wherein non-neighboring methylene units may be replaced by —O—, —COO—, —COO— or —OCOO— radicals;

n is a number ranging from 1 to 4,000;

a is a number of at least 1;

b is a number ranging from 0 to 40;

c is a number ranging from 0 to 30; and d is a number greater than 0, on condition that A is an NH radical in at least one of the (a) units.

By way of non-limiting example R can be a monovalent hydrocarbon-based radical with 1 to 6 carbon atoms, including methyl, ethyl, vinyl and phenyl. In at least one embodiment, R is an unsubstituted alkyl radical.

By way of non-limiting example, X can be an alkylene radical with 2 to 10 carbon atoms. In at least one embodiment, the alkylene radical X is uninterrupted.

By way of non-limiting example, in at least one embodiment, the A group in all the (b) and (c) units, when they are present, is NH.

In at least one embodiment, all the A groups are NH radicals.

By way of non-limiting example, Z can be an oxygen atom or an NH radical.

By way of non-limiting example, Y can be a hydrocarbon-based radical comprising from 3 to 13 carbon atoms, and, in at least one embodiment, not substituted. For instance, Y may be chosen from a linear, cyclic aralkylene, or alkylene radical.

By way of non-limiting example, D can be an alkylene radical with 2 to 12 carbon atoms, for example from 4 to 12 carbon atoms.

In at least one embodiment, D is a polyoxyalkylene radical, including but not limited to a polyoxyethylene or polyoxypropylene radical with 20 to 800 carbon atoms, for example 100 to 200 carbon atoms.

In at least one embodiment, the D radical is not substituted.

By way of non-limiting example, n can be a number ranging from 3 to 800, for example from 25 to 400 or from 25 to 250.

By way of non-limiting example, a can be a number of more than 50.

By way of non-limiting example, when b is a number other than 0, b can be a number of at most 50, for example at most 25.

By way of non-limiting example, c can be a number of at most 10, and in at least one embodiment for example at most 5.

The copolymers of the present disclosure may be obtained according to the polymerization processes described for instance, in U.S. Patent Application Publication No. 2004/0254325 or International Patent Application Publication No. 03/014194.

The copolymer may thus be obtained by a two-step process, such that:

in the first step, a silazane of formulae (2) or (2'):

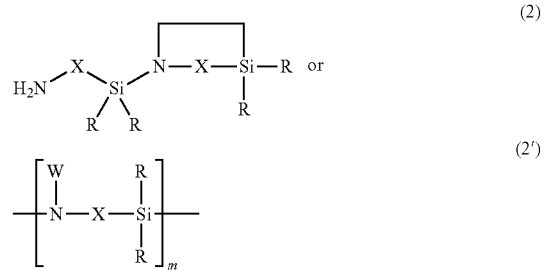

W being chosen from hydrogen, substituted and unsubstituted hydrocarbon-based radicals, for instance comprising from 1 to 20 carbon atoms, and $R_2Si$—X—$NH_2$ radicals;

is reacted with an organic silicon compound of formula (3):

$$(HO)(R_2SiO)_{n-1}[H] \tag{3}$$

obtaining an aminoalkylpolydiorganosiloxane of formula (4):

$$H_2N-X-[SiR_2O]_nSiR_2-X-NH_2 \tag{4; and}$$

in a second step, the aminoalkylpolydiorganosiloxane of formula (4) is polymerized with a diisocyanate of formula (5):

$$OCN-Y-NCO \tag{5}$$

Generally, in the first step, the silazanes of formulae (2) or (2') and the reactants containing silanol groups are used in equimolar ratios.

For the preparation of very pure bisaminoalkyl-terminated silicones of formula (4), a small excess of the silazane compound of formulae (2) or (2') is for instance used, which can then be removed in a simple supplementary process step such as, for example, the addition of small amounts of water.

When b is at least 1, it is possible to use, during the second step, up to 95% by weight, based on all the components used, of chain extenders, chosen from diamines, hydroxyl compounds blocked by an isocyanate, dihydroxyl compounds or mixtures thereof.

For example, the chain extenders can be chosen from those of formula (6):

$$HZ\text{-}D\text{-}ZH \tag{6}$$

wherein D and Z have the meanings disclosed herein. When Z stands for O, the chain extender of formula (6) may also be reacted, before the reaction in the second step, with the diisocyanate of formula (5). Where appropriate, it is possible to use water as a chain extender.

Non-limiting examples of diisocyanates of formula (5) that may be used, are aliphatic compounds such as isophoronediisocyanate, hexamethylene-1,6-diisocyanate, tetramethylene-1,4-diisocyanate and methylenedicyclohexyl-4,4'-diisocyanate or aromatic compounds such as methylenediphenyl-4,4'-diisocyanate, 2,4-toluenediisocyanate, 2,5-toluenediisocyanate, 2,6-toluenediisocyanate, m-phenylenediisocyanate, p-phenylenediisocyanate, m-xylenediisocyanate, tetramethyl-m-xylenediisocyanate or mixtures of these isocyanates. A non-limiting example of a commercially available compound is a diisocyanate from the DESMODUR® series (H, I, M, T, W) from Bayer AG, Germany. Aliphatic diisocyanates wherein Y is an alkylene radical may result in materials that have improved UV stabilities.

Other examples of the α,ω-OH terminated alkylenes of formula (6) include but are not limited to polyalkylenes or polyoxyalkylenes. These may generally be devoid of contamination by monofunctional polyoxyalkylenes, trifunctional polyoxyalkylenes or polyoxyalkylenes of higher functionality. Non-limiting examples also include polyether polyols, polytetramethylene diols, polyester polyols, and polycaprolactone diols and α,ω-OH terminated polyalkylenes based on poly(vinyl acetate), poly(vinyl acetate)/ethylene copolymers, poly(vinyl chloride) copolymers or polyisobutylene diols. Non-limiting examples which may be used are polyoxyalkyls, for instance polypropylene glycols. Such compounds are available commercially as base materials, inter alia, for polyurethane foams and for instance can be used as coatings with molecular weights Mn of up to 10,000. Non-limiting examples include the BAYCOLL® polyether polyols and polyester polyols from Bayer AG, Germany, or the ACCLAIM® polyether polyols from Lyondell Inc., USA. Non-limiting examples which may be used are α,ω-alkylene diol monomers, such as ethylene glycol, propanediol, butanediol or hexanediol. Furthermore, as used herein the term "dihydroxylated compounds" means bishydroxyalkylsilicones, such as those supplied, for example, by Goldschmidt under the names TEGOMER H-Si 2111, 2311 and 2711.

The preparation of the copolymers disclosed herein of formula (I) can be carried out in solution but also in a solid form, continuously or batchwise.

If the amount of urethane or urea segments is large, a solvent having a high solubility parameter, such as, for example, dimethylacetamide, can be chosen. For instance, THF may be used. In at least one embodiment, the synthesis of the copolymer can be carried out without solvent.

The synthesis can be carried out in the absence of moisture and under a protective gas, for instance nitrogen or argon.

The reaction can be carried out in the presence of a catalyst. The catalysts suitable for the preparation can be dialkyltin compounds, such as, for example, dibutyltin dilaurate or dibutyltin diacetate, or tertiary amines, such as, for example, N,N-dimethylcyclohexaneamine, 2-dimethylaminoethanol or 4-dimethylaminopyridine.

In at least one embodiment, the copolymer of the present disclosure does not comprise polyurethane.

By way of non-limiting example, the copolymer can be a non-ionic polysiloxane/polyurea copolymer, that is to say that it does not comprise an ionized or ionizable group.

By way of example of a copolymer, non-limiting mention may be made of the dimethylpolysiloxane/urea copolymer having the INCI name polyureadimethicone.

Such a polymer can be obtained, for instance, by a copolymerization of an α,ω-aminosilicone with a diisocyanate. Polymers corresponding to these characteristics are, for example, the products sold under the reference Wacker-Belsil® UD 60, Wacker-Belsil® UD 80, Wacker-Belsil® UD 140 and Wacker-Belsil® UD 200 by Wacker.

In at least one embodiment, the polysiloxane/polyurea copolymer is non-ionic.

The at least one polysiloxane/polyurea block copolymer can be present in an amount ranging from 0.05 to 20%, for example from 0.1 to 15% or from 0.5 to 10% of the weight of the composition applied.

Filler

The composition may contain at least one filler, which is chosen from substantially colorless compounds that are solid at ambient temperature and atmospheric pressure and that are insoluble in the composition, even when these ingredients are brought to a temperature greater than ambient temperature.

The fillers may be inorganic or organic. The fillers may be particles of any shape, including platelet, spherical or oblong particles, whatever their crystallographic form (for example, sheet, cubic, hexagonal, orthorhombic). Moreover, these particles may be solid, hollow or porous and coated or uncoated.

Non-limiting mention may in particular be made, among the fillers which can be used in the compositions according to the present disclosure as inorganic fillers include talc, natural or synthetic mica; silica, kaolin, boron nitride, precipitated calcium carbonate, magnesium carbonate, basic magnesium carbonate and hydroxyapatite.

These inorganic fillers can be in the form of spherical particles with, for example, hollow silica microspheres, such as the SILICA BEADS SB 700/HA® or SILICA BEADS SB 700® from Maprecos or the SUNSPHERES H-33® and SUNSPHERES H-51® from Asahi Glass.

The inorganic particles may exhibit a number-average primary size ranging from 0.1 to 30 μm, for example from 0.2 to 20 μm or from 0.5 to 15 μm. As used herein, the term "primary particle size" means the maximum dimension which it is possible to measure between two diametrically opposite points of an individual particle. The size of the organic particles can be determined by transmission electron microscopy or from the measurement of the specific surface area by the BET method or from laser particle size analysis.

In at least one embodiment, the inorganic fillers include but are not limited to silica, talc, and boron nitride.

Non-limiting mention may be made, among these fillers which can be used in the compositions according to the present disclosure, of organic fillers. As used herein, the term "organic filler" means a polymeric particle which can result from the polymerization of at least one monomer. The polymers comprising these organic particles may or may not be crosslinked. The monomers used can be, for example, methacrylic or acrylic acid esters, such as methyl acrylate and methyl methacrylate, vinylidene chloride, acrylonitrile or styrene and derivatives thereof.

The organic particles may exhibit a number-average primary size ranging from 1 to 30 μm, for example from 1 to 20 μm or from 1 to 15 μm.

The organic particles used in the cosmetic composition according to the present disclosure can be chosen from but are not limited to polyamide powders, acrylic polymer powders, for instance polymethyl methacrylate powders, powders of acrylic copolymers, for example polymethyl methacrylate/ethylene glycol dimethacrylate, of polyallyl methacrylate/ethylene glycol dimethacrylate, of ethylene glycol dimethacrylate/lauryl methacrylate copolymer or of polyacrylate/alkyl acrylate, polystyrene powders, polyethylene powders, for example polyethylene/acrylic acid powders, and silicone resin microbeads.

Non-limiting mention may in particular be made, by way of representation and without applied limitation, as organic particles according to the present disclosure, of:

polyamide (Nylon®) powders, for example those sold under the names ORGASOL® 4000 and ORGASOL® 2002 UD NAT COS 204 by Atochem;

acrylic polymer powders, including polymethyl methacrylate powders, such as, for example, those sold under the name COVABEAD® LH85 or COVABEAD® PMMA by Wacker or those sold under the name MICROPEARL® MHB" by Matsumoto;

acrylic copolymer powders, including polymethyl methacrylate/ethylene glycol dimethacrylate powders, such as those sold under the name of DOW CORNING 5640 MICROSPONGE® SKIN OIL ADSORBER by Dow Corning or those sold under the name GANZPEARL® GMP-0820 by Ganz Chemical, polyallyl methacrylate/ethylene glycol dimethacrylate powders, such as those sold under the name POLYPORE® L200 or POLYPORE® E200 by Amcol, ethylene glycol dimethacrylate/lauryl methacrylate copolymer powders, such as those sold under the name POLYTRAP® 6603" by Dow Corning, or polyacrylate/ethylhexyl acrylate powders, such as those sold under the name TECHPOLYMER® ACX 806C by Sekisui;

polystyrene/divinylbenzene powders, such as those sold under the name TECHPOLYMER® SBX8 by Sekisui;

polyethylene powders, including polyethylene/acrylic acid powders, sold under the name FLOBEADS® by Sumitomo;

silicone resin microbeads, such as those sold under the names TOSPEARL® by Toshiba Silicone, including TOSPEARL® 240A and TOSPEARL® 120A;

acrylic polymer microspheres, such as those made of crosslinked acrylate copolymer, POLYTRAP 6603 ADSORBER® from RP Scherrer;

polyurethane powders, such as the hexamethylene diisocyanate/trimethylol hexyllactone copolymer powder sold under the name PLASTIC POWDER D-400® by Toshiki;

methyl acrylate or methacrylate polymer or copolymer microcapsules or else vinylidene chloride/acrylonitrile copolymer microcapsules, such as EXPANCEL® from Expancel;

crosslinked organopolysiloxane elastomer powders, such as those sold under the name TREFIL POWDER E-506C by Dow Corning; and polyfluorinated powders, including polytetrafluoroethylene powder, for example that sold under the name MP 1400 by DuPont de Nemours.

The organic particles used in the composition in accordance with the present disclosure are chosen from polyamide powders and polymethyl methacrylate powders.

The at least one filler can be present in the composition in an amount ranging from 0.001 to 20% by weight of the total weight of the composition, for example ranging from 0.1 to 10%.

The composition of the present disclosure may also comprise at least one colored or coloring entity such as colored pigments, hydrophilic or hydrophobic direct dyes or dye precursors. The colored pigments and the dyes may or may not be fluorescent.

The at least one colored or coloring entity can be present in the composition in an amount ranging from 0.001 to 20% by weight of the total weight of the composition, for example ranging from 0.1 to 10%.

As used herein, the term "colored entity" means a compound that is colored in the dry state or in solution, that is to say which absorbs in the range from 250 to 750 nm and/or which re-emits visible light by excitation. As used herein, the term "coloring entity" means an uncolored entity that generates at least one colored compound by interaction with a reactive agent, such as an oxidizing agent.

Non-limiting examples of hydrophilic dyes, include dyes exhibiting a hydrophilicity defined by the log P value of less than or equal to 2. In the context of the present disclosure, the log P value conventionally represents the partition coefficient of the dye between octanol and water. The log P value can be calculated according to the method described in the paper by Meylan and Howard, "Atom/fragment contribution method for estimating octanol-water partition coefficient," J. Pharm. Sci., 1995, 84, pp. 83-92. This value can also be calculated from numerous commercially available software packages which determine the log P value as a function of the structure of a molecule.

Non-limiting mention may be made, by way of example, of the Epiwin software of the US Environmental Protection Agency.

In at least one embodiment, log P of the hydrophilic dyes in the composition of the present disclosure can be less than 2.

Non-limiting mention may be made, among these hydrophilic dyes, of neutral, acid or cationic nitrobenzene direct dyes; neutral, acid or cationic azo direct dyes; neutral, acid or cationic quinone and such as anthraquinone direct dyes; azine direct dyes; triarylmethane direct dyes; indoamine direct dyes and natural direct dyes.

Thus, the direct dyes can be chosen as a function of the log P value. Further non-limiting mention can be made of:

| STRUCTURE | NAME | log P |
|---|---|---|
| (structure: benzene ring with NH$_2$, NH$_2$, NO$_2$ substituents) | 4-nitro-o-phenylenediamine | 0.88 |
| (structure: benzene ring with NH$_2$, NO$_2$, NH$_2$ substituents) | 2-nitro-p-phenylenediamine | 0.53 |

-continued

| STRUCTURE | NAME | log P |
|---|---|---|
| (structure) | picramic acid | 0.93 |
| (structure) | HC Red 13 | 0.66 |
| (structure) | N,N'-bis(2-hydroxyethyl)-2-nitro-p-phenylenediamine | −0.44 |
| (structure) | HC Red 7 | 0.13 |
| (structure) | HC Blue 2 | −0.32 |
| (structure) | HC Yellow 4 | 0.56 |
| (structure) | HC Yellow 2 | 1.05 |

-continued
| STRUCTURE | NAME | log P |
|---|---|---|
| 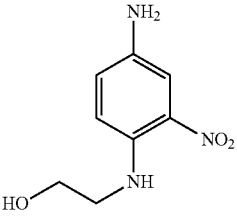 [SMILES: Nc1ccc(NCCO)c([N+](=O)[O-])c1] | HC Red 3 | −0.42 |
| 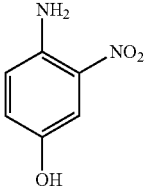 [SMILES: Nc1ccc(O)cc1[N+](=O)[O-]] | 4-amino-3-nitrophenol | 1.19 |
| 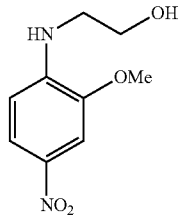 [SMILES: COc1cc([N+](=O)[O-])ccc1NCCO] | 1-hydroxyethylamino-5-nitroanisole | 1.13 |
| 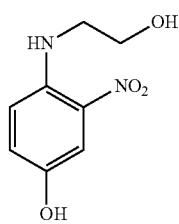 [SMILES: O=[N+]([O-])c1cc(O)ccc1NCCO] | 3-nitro-p-(hydroxyethylamino)-phenol | 0.21 |
| 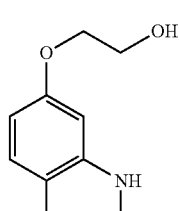 | 3-methylamino-4-nitrophenoxyethanol | 1.13 |
| 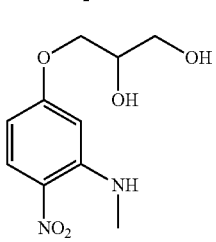 | 2-nitro-5-(glyceryl)methylaniline | 0.89 |
| 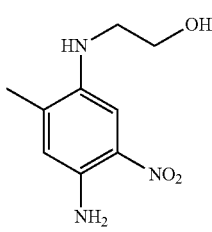 | HC Violet 1 | 0.67 |

| STRUCTURE | NAME | log P |
|---|---|---|
| (structure) | HC Orange 2 | 0.15 |
| (structure) | HC Yellow 9 | 1.12 |
| (structure) | 4-nitrophenylamino-ethylurea | 0.59 |
| (structure) | HC Red 10 and HC Red 11 | 0.13 |
| (structure) | 2-hydroxyethylpicramic acid | 0.38 |
| (structure) | HC Blue 12 | 1.15 |

-continued

| STRUCTURE | NAME | log P |
|---|---|---|
| 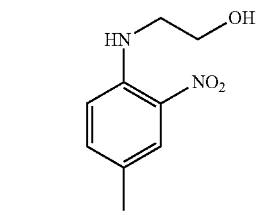 | 3-nitro-4-(N-(β-hydroxyethyl)-amino)toluene | 1.59 |
| | 2-(N-(β-methoxyethyl)amino)-5-N,N-bis(hydroxyethyl)aminonitrobenzene | 0.38 |
| 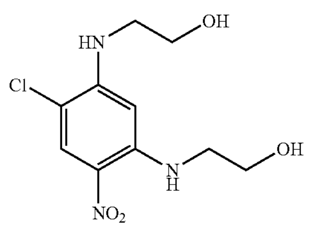 [SMILES: O=[N+]([O-])c1cc(Cl)c(NCCO)cc1NCCO] | HC Yellow 10 | 0.20 |
| 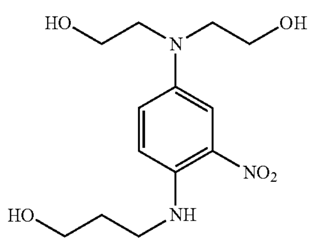 [SMILES: O=[N+]([O-])c1cc(N(CCO)CCO)ccc1NCCCO] | HC Violet 2 | 0.17 |
| 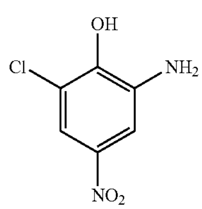 [SMILES: Nc1cc([N+](=O)[O-])cc(Cl)c1O] | 2-amino-6-chloro-4-nitrophenol | 1.53 |
| 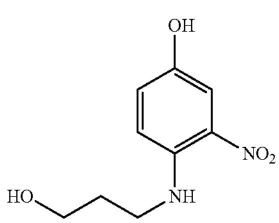 [SMILES: O=[N+]([O-])c1cc(O)ccc1NCCCO] | 4-hydroxypropylamino-3-nitrophenol | 0.70 |
| 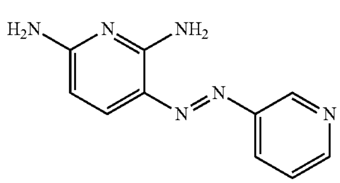 [SMILES: Nc1ccc(/N=N/c2cccnc2)c(N)n1] | 2,6-diamino-3-((pyridine-3-yl)azo)pyridine | 1.58 |

| STRUCTURE | NAME | log P |
|---|---|---|
| [structure: H₂N-C₆H₄-N=N-C₆H₄-N(CH₂CH₂OH)₂] | Disperse Black 9 | 1.83 |
| [structure: anthraquinone with two HN-CH₂-CH(OH)-CH₂OH substituents] | HC Blue 14 | 0.62 |

The composition of the disclosure can also comprise hydrophobic dyes. In the context of the present disclosure, the hydrophobicity is defined by the log P value, which may be greater than 2.

Non-limiting mention may be made, by way of example, of:

| Dye | Chemical structure | log P |
|---|---|---|
| Solvent Black 3 | [structure] | 8.81 |
| Solvent Blue 104 | [anthraquinone with two mesitylamino groups] | 8.26 |
| Disperse Blue 134 | [anthraquinone with two isopropylamino groups] | 6.07 |

-continued

| Dye | Chemical structure | log P |
|---|---|---|
| Solvent Blue 14 | 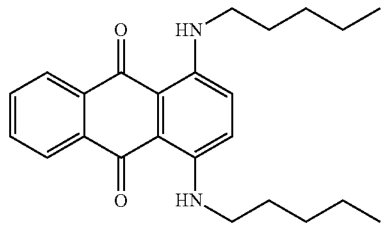 [SMILES: CCCCCNc1ccc(NCCCCC)c2c1C(=O)c1ccccc1C2=O] | 8.18 |
| Disperse Blue 14 | 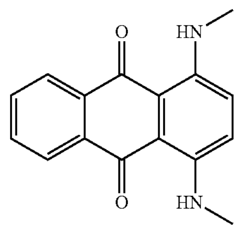 [SMILES: CNc1ccc(NC)c2c1C(=O)c1ccccc1C2=O] | 4.25 |
| Solvent Red 2 | 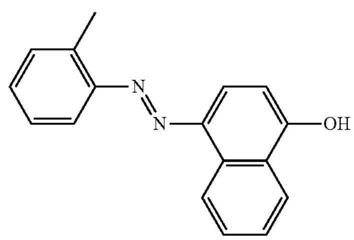 [SMILES: Cc1ccccc1/N=N/c1ccc(O)c2ccccc12] | 5.35 |
| Solvent Brown 5 | 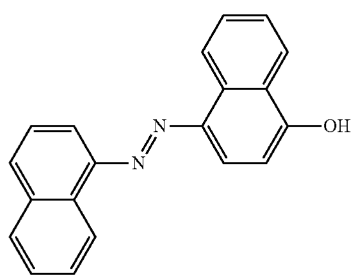 [SMILES: Oc1ccc(/N=N/c2cccc3ccccc23)c2ccccc12] | 5.98 |
| Solvent Green 5 | 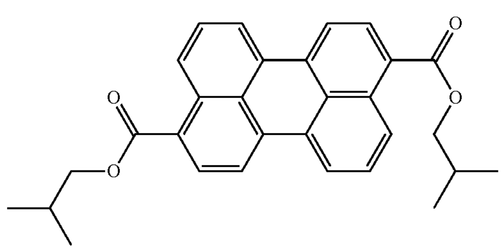 [SMILES: CC(C)COC(=O)c1ccc2c3cccc4c(C(=O)OCC(C)C)ccc(c5cccc1c52)c43] | 8.55 |
| Solvent Orange 2 | 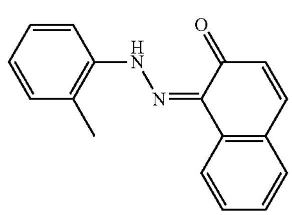 [SMILES: Cc1ccccc1N/N=C1\C(=O)C=Cc2ccccc21] | 3.86 |
| Solvent Orange 1 | 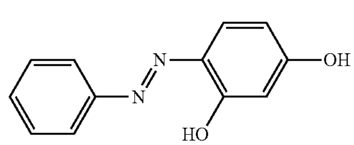 [SMILES: Oc1ccc(/N=N/c2ccccc2)c(O)c1] | 3.85 |

-continued

| Dye | Chemical structure | log P |
|---|---|---|
| Disperse Orange 24 | 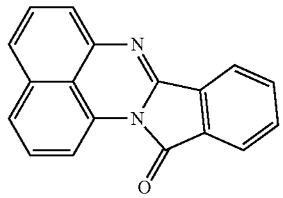 [SMILES: O=C1c2ccccc2C2=Nc3cccc4cccc(c34)N12] | 3.21 |
| Solvent Orange 63 | 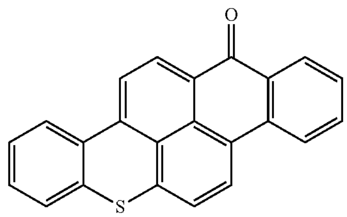 [SMILES: O=c1c2ccccc2c2ccc3sc4ccccc4c4ccc1c2c34] | 7.02 |
| Solvent Red 49 | 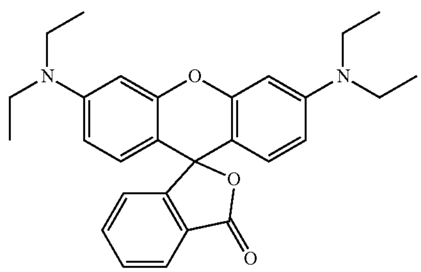 [SMILES: CCN(CC)c1ccc2c(c1)Oc1cc(N(CC)CC)ccc1C21OC(=O)c2ccccc21] | 6.63 |
| Solvent Red 1 | 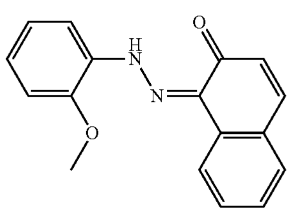 [SMILES: COc1ccccc1N/N=C1\C(=O)C=Cc2ccccc21] | 3.39 |
| Solvent Red 26 | 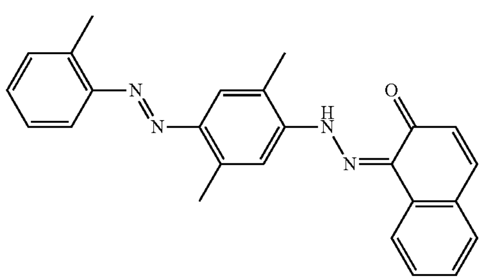 [SMILES: Cc1ccccc1/N=N/c1cc(C)c(N/N=C2\C(=O)C=Cc3ccccc32)cc1C] | 7.07 |
| Solvent Red 27 | 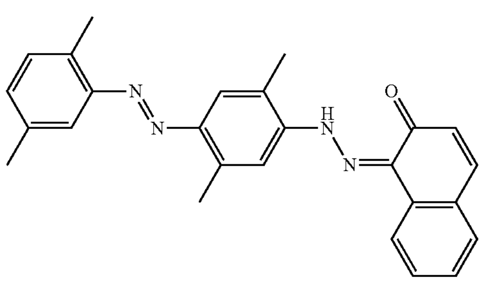 [SMILES: Cc1ccc(C)c(/N=N/c2cc(C)c(N/N=C3\C(=O)C=Cc4ccccc43)cc2C)c1] | 7.62 |

-continued

| Dye | Chemical structure | log P |
|---|---|---|
| Solvent Red 18 | 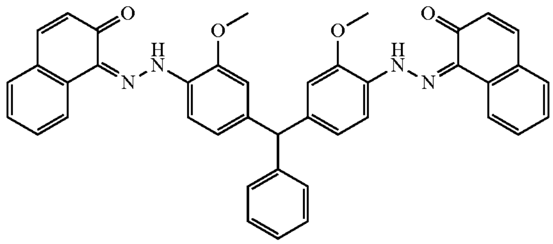 [SMILES: COc1cc(C(c2ccccc2)c2ccc(N/N=C3\C(=O)C=Cc4ccccc43)c(OC)c2)ccc1N/N=C1\C(=O)C=Cc2ccccc21] | 8.16 |
| Solvent Red 23 | 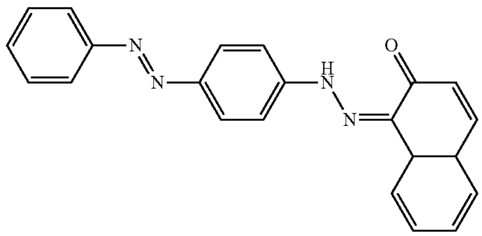 [SMILES: O=C1C=CC2C=CC=CC2/C1=N/Nc1ccc(/N=N/c2ccccc2)cc1] | 5.58 |
| Solvent Red 4 | 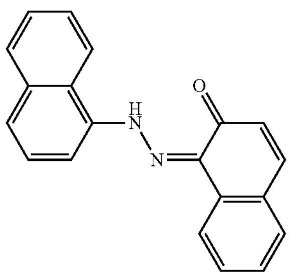 [SMILES: O=C1C=Cc2ccccc2/C1=N/Nc1cccc2ccccc12] | 4.48 |
| Solvent Orange 7 | 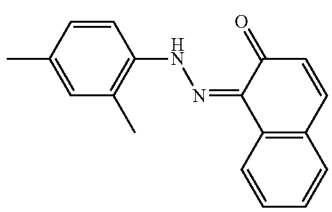 [SMILES: Cc1ccc(N/N=C2\C(=O)C=Cc3ccccc32)c(C)c1] | 4.40 |
| Disperse Blue 72 | 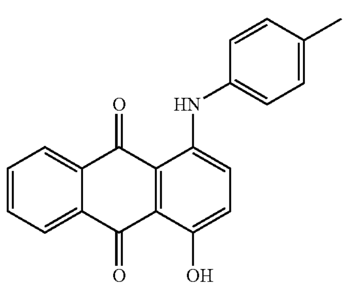 [SMILES: Cc1ccc(Nc2ccc(O)c3c2C(=O)c2ccccc2C3=O)cc1] | 6.24 |

-continued

| Dye | Chemical structure | log P |
|---|---|---|
| Disperse Violet 26 | 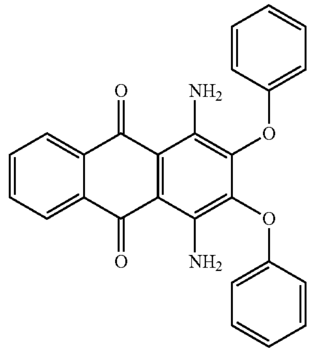 [SMILES: Nc1c(Oc2ccccc2)c(Oc2ccccc2)c(N)c2c1C(=O)c1ccccc1C2=O] | 5.19 |
| Disperse Yellow 16 | 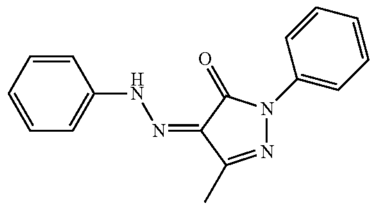 [SMILES: CC1=NN(c2ccccc2)C(=O)/C1=N\Nc1ccccc1] | 3.89 |
| Disperse Yellow 82 | 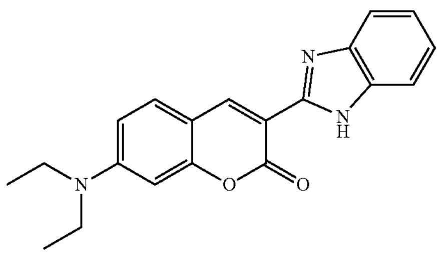 [SMILES: CCN(CC)c1ccc2cc(-c3nc4ccccc4[nH]3)c(=O)oc2c1] | 3.68 |
| Disperse Yellow 54 | 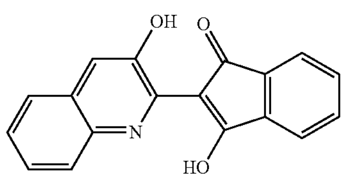 [SMILES: O=C1C(c2nc3ccccc3cc2O)=C(O)c2ccccc21] | 4.76 |
| Solvent Yellow 29 | 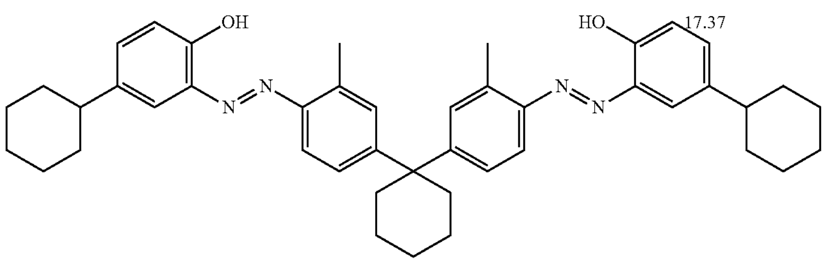 [SMILES: Cc1cc(C2(c3ccc(/N=N/c4cc(C5CCCCC5)ccc4O)c(C)c3)CCCCC2)ccc1/N=N/c1cc(C2CCCCC2)ccc1O] | 17.37 |
| Solvent Yellow 163 | 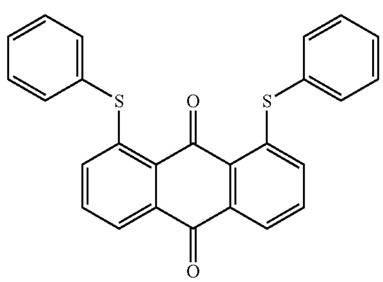 [SMILES: O=C1c2cccc(Sc3ccccc3)c2C(=O)c2c(Sc3ccccc3)cccc21] | 7.94 |

-continued
| Dye | Chemical structure | log P |
|---|---|---|
| Solvent Yellow 3 | 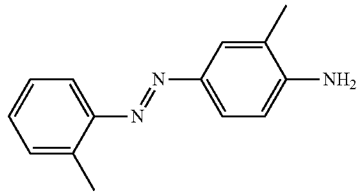 [SMILES: Cc1cc(/N=N/c2ccccc2C)ccc1N] | 4.29 |
| Solvent Yellow 56 | 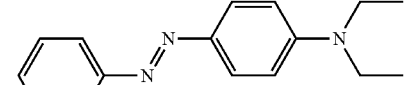 | 5.27 |
| Solvent Yellow 18 | 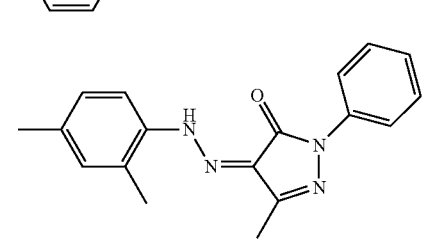 | 4.98 |
| Solvent Yellow 98 | 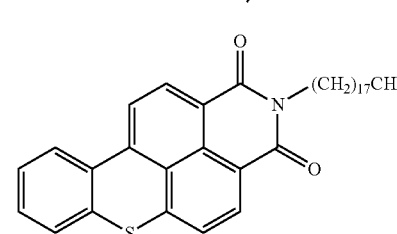 | 4.5 |
| Solvent Yellow 12 | 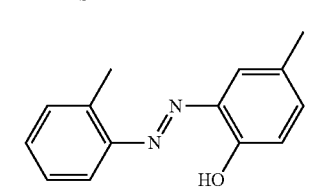 | 5.43 |
| Solvent Yellow 14 | 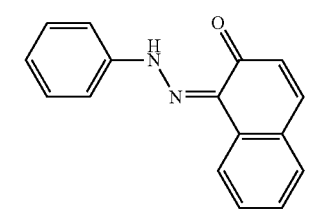 | 3.31 |
| Disperse Red 13 | 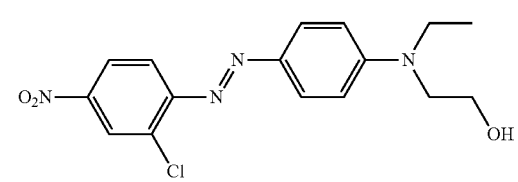 [SMILES: CCN(CCO)c1ccc(/N=N/c2ccc([N+](=O)[O-])cc2Cl)cc1] | 5.22 |
| Disperse Green 9 | 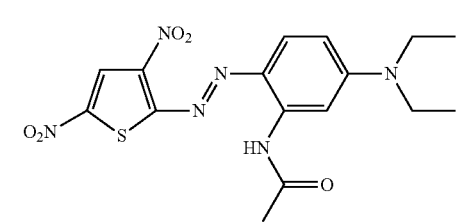 [SMILES: CCN(CC)c1ccc(/N=N/c2sc([N+](=O)[O-])cc2[N+](=O)[O-])c(NC(C)=O)c1] | 4.23 |

-continued

| Dye | Chemical structure | log P |
|---|---|---|
| Disperse Blue 148 | 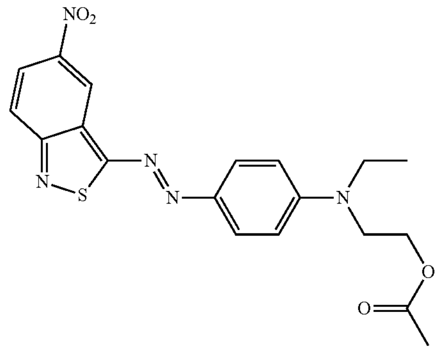 [SMILES: CCN(CCOC(C)=O)c1ccc(/N=N/c2snc3ccc([N+](=O)[O-])cc23)cc1] | 4.81 |
| Disperse Violet 63 | 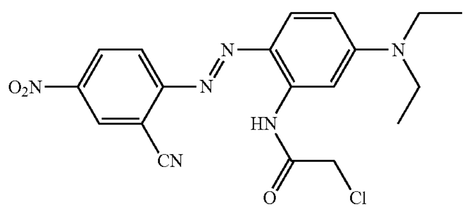 [SMILES: CCN(CC)c1ccc(/N=N/c2ccc([N+](=O)[O-])cc2C#N)c(NC(=O)CCl)c1] | 5.30 |
| Disperse Blue 60 | 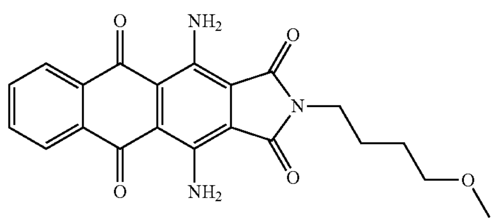 [SMILES: COCCCCn1c(=O)c2c(N)c3c(=O)c4ccccc4c(=O)c3c(N)c2c1=O] | 3.38 |
| Solvent Orange 15 | 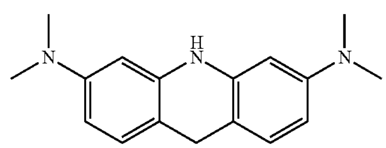 | 3.90 |

In at least one embodiment, the hydrophobic dyes have a log P of greater than 4 or greater than 6.

The use of fluorescent dyes can make it possible to obtain, on dark hair, colorings which are more visible than with conventional hydrophilic or hydrophobic direct dyes. Furthermore, these fluorescent dyes, when they are applied to dark hair, can also make it possible to lighten it without damaging it. This technique, disclosed for example in French Patent No. FR 2,830,189, can make it possible to be kind to the quality of the keratin fiber during the treatment, but the fluorescent dyes employed do not always exhibit good resistance to shampooing operations. The presence of the PDMS/polyurea copolymer of the present disclosure can make it possible to improve this persistence towards shampooing operations.

As included herein, the term "fluorescent compound" means fluorescent dyes and optical brighteners. These fluorescent compounds themselves also are soluble in the medium of the composition.

Fluorescent dyes are fluorescent compounds which absorb visible radiation, generally ranging from 400 to 800 nm, and which are capable of re-emitting light in the visible region at a higher wavelength. By definition, these dyes are colored entities since they absorb visible light.

In at least one embodiment, the fluorescent dyes re-emit orange-colored fluorescent light. They exhibit a re-emission wavelength ranging from 500 to 700 nm.

Non-limiting mention may be made, as examples of fluorescent dyes, of the compounds known from the art, for example disclosed in: Ullmann's Encyclopedia of Industrial Chemistry, Release 2004, 7th edition, "Fluorescent Dyes" chapter.

The optical brighteners of the present disclosure, also known under the name of "brighteners," or "fluorescent brighteners," or "fluorescent brightening agents" or "FWAs," or "fluorescent whitening agents," or "whiteners," or "fluorescent whiteners," are colorless transparent compounds as they do not absorb in visible light but only in ultraviolet light (wavelengths ranging from 200 to 400 nanometers) and convert the energy absorbed into fluorescent light of higher wavelength emitted in the visible part of the spectrum, generally in the blue and/or green, that is to say in wavelengths ranging from 400 to 550 nanometers.

Optical brighteners are known in the art. They are, for example, described in Ullmann's Encyclopedia of Industrial Chemistry (2002), "Optical Brighteners" and Kirk-Othmer Encyclopedia of Chemical Technology (1995): "Fluorescent Whitening Agents."

The fluorescent dyes which can be used in the context of the present disclosure are compounds known in the art. They are, for example, described in French Patent No. FR 2,830,189. Non-limiting mention may in particular be made, as examples of fluorescent dyes:

Photosensitizing Dye NK 557, sold by Ubichem, with the following structure:

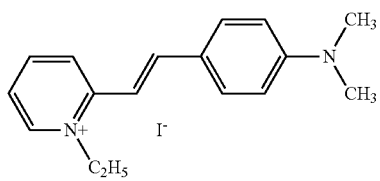

2-[2-(4-(dimethylamino)phenyl)ethenyl]-1-ethylpyridinium iodide;

Brilliant Yellow B6GL, sold by Sandoz with the following structure:

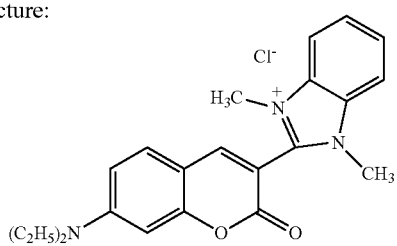

Basic Yellow 2, or Auraminoe O sold by Prolabo, Aldrich or Carlo Erba with the following structure:

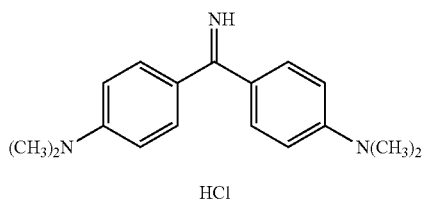

4,4' (imidocarbonyl)bis(N,N-dimethylaniline) monohydrochloride

Further non-limiting examples, as optical brighteners and fluorescent dyes include:

naphthalimides, for example the following compound:

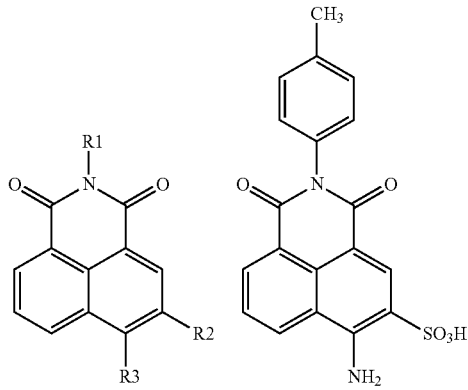

Brillant sulphoflavin FF, C.I. 56205 wherein R1, R2 and R3 which may be identical or different, are chosen from hydrogen; a halogen atom; a $C_6$-$C_{30}$ aryl group; a hydroxyl group; a cyano group; a nitro group; a sulpho group; an amino group; an acylamino group; a di($C_1$-$C_6$)alkylamino group; a dihydroxy($C_1$-$C_6$)alkylamino group; a ($C_1$-$C_6$)alkylhydroxy($C_1$-$C_6$)alkylamino group; a ($C_1$-$C_6$)alkoxy group; a ($C_1$-$C_6$)alkoxycarbonyl group; a carboxy($C_1$-$C_6$)alkoxy group; a piperidinosuiphonyl group; a pyrrolidino group; a ($C_1$-$C_6$)alkylhalo($C_1$-$C_6$)alkylamino group; a benzoyl($C_1$-$C_6$)alkyl group; a vinyl group; a formyl group; a $C_6$-$C_{30}$ aryl radical optionally substituted by at least one group chosen from a hydroxyl group, a linear, branched or cyclic $C_1$-$C_6$ alkoxy group or a linear, branched or cyclic alkyl group comprising from 1 to 22 carbon atoms, itself optionally being substituted by at least one hydroxyl, amino or $C_1$-$C_6$ alkoxy group; a linear, branched or cyclic alkyl radical comprising from 1 to 22 carbon atoms, for example from 1 to 6 carbon atoms, optionally substituted by at least one group chosen from hydroxyl, amino, linear, branched or cyclic $C_1$-$C_6$ alkoxy, optionally substituted aryl, carboxyl or sulpho groups or a halogen, it being possible for this alkyl radical to be interrupted by a heteroatom, such as N, S or O; the R1, R2 and R3 substituents can form, with the carbon atoms to which they are attached, a $C_6$-$C_{30}$ aromatic or non-aromatic ring or a heterocyclic ring comprising, in total, from 5 to 30 ring members and from 1 to 5 heteroatoms; these rings being fused or non-fused and inserting or not inserting a carbonyl group and being unsubstituted or substituted by at least one group chosen from $C_1$-$C_4$ alkyl, ($C_1$-$C_4$)alkoxy($C_1$-$C_4$)alkyl, amino, di($C_1$-$C_4$)alkylamino, halogen, phenyl, carboxyl or tri($C_1$-$C_4$)alkylammonio($C_1$-$C_4$)alkyl groups.

Coumarin derivatives, such as the compounds of the following formula:

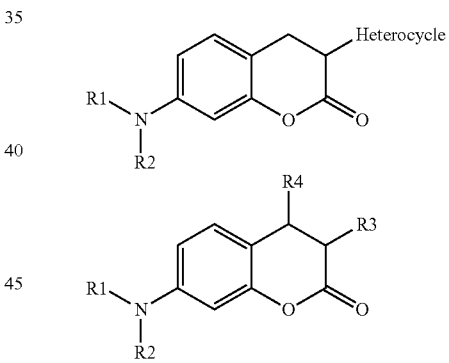

wherein the heterocycle is chosen from furan, thiophene, 2H-pyrrole, 2-pyrroline, pyrrolidine, 1,3-dioxolane, oxazole, thiazole, imidazole, 2-imidazoline, imidazoline, pyrazole, 2-pyrazoline, pyrazolidine, isoxazole, isothiazole, 1,2,3-oxadiazole, 1,2,3-triazole, 1,3,4-thiadiazole, 2H-pyran, 4H-pyran, pyridine, piperidine, 1,4-dioxane, morpholine, 1,4-dithiane, thiomorpholine, pyridazine, pyrimidine, pyrazine, piperazine, 1,3,5-triazine, 1,3,5-trithiane, indolizine, indole, isoindole, 3H-indole, indoline, benzo[b]furan, benzo[b]thiophene, 1H-indazole, benzimidazole, benzothiazole, purine, 4H-quinolizine, quinoline, isoquinoline, cinnoline, phthalazine, quinazoline, quinoxaline, 1,8-naphthyridine, pteridine, quinuclidine, carbazole, acridine, phenazine, phenothiazine, phenoxazine, indene, naphthalene, azulene, fluorene, anthracene, norbornane, adamantane, and wherein R1, R2, R3 and R4 which may be identical or different, are chosen from hydrogen; a halogen atom; a $C_6$-$C_{30}$ aryl group; a hydroxyl group; a cyano group; a nitro group; a sulpho group; an amino group; an acylamino group; a di($C_1$-$C_6$)alkylamino group; a dihydroxy($C_1$-$C_6$)alkylamino group; a ($C_1$-$C_6$)alkylhydroxy($C_1$-$C_6$)alkylamino group; a ($C_1$-$C_6$)alkoxy group; a ($C_1$-$C_6$)alkoxycarbonyl group; a carboxy($C_1$-$C_6$)alkoxy group; a piperidinosulphonyl group; a pyrrolidino group; a ($C_1$-$C_6$)alkylhalo($C_1$-$C_6$)alkylamino group; a benzoyl($C_1$-$C_6$)alkyl group; a vinyl group; a formyl group; a $C_6$-$C_{30}$ aryl radical optionally substituted by at least one group chosen from a hydroxyl group, a linear, branched or cyclic $C_1$-$C_6$ alkoxy group or a linear, branched or cyclic alkyl group comprising from 1 to 22 carbon atoms, itself optionally being substituted by at least one hydroxyl, amino or $C_1$-$C_6$ alkoxy group; a linear, branched or cyclic alkyl radical comprising from 1 to 22 carbon atoms, for example from 1 to 6 carbon atoms, optionally substituted by at least one group chosen from hydroxyl, amino, linear, branched or cyclic $C_1$-$C_6$ alkoxy, optionally substituted aryl, carboxyl or sulpho groups or a halogen, it being possible for this alkyl radical to be interrupted by a heteroatom, such as a nitrogen, sulfur or oxygen atom; the R1, R2, R3 and R4 substituents can form, with the carbon atoms to which they are attached, a $C_6$-$C_{30}$ aromatic or non-aromatic ring or a heterocyclic ring comprising, in total, from 5 to 30 ring members and from 1 to 5 heteroatoms; these rings being fused or non-fused and inserting or not inserting a carbonyl group and being unsubstituted or substituted by at least one group chosen from $C_1$-$C_4$ alkyl, ($C_1$-$C_4$)alkoxy($C_1$-$C_4$)alkyl, amino, di($C_1$-$C_4$)alkylamino, halogen, phenyl, carboxyl or tri($C_1$-$C_4$)alkylammonio($C_1$-$C_4$)alkyl groups;

two of the R3 and R4 substituents can form, with the carbon atoms to which they are attached, a $C_6$-$C_{30}$ aromatic ring or a heterocyclic ring comprising, in total, from 5 to 30 ring members and from 1 to 5 heteroatoms; this ring being fused or non-fused, this ring and the possible fused ring being unsubstituted or substituted by at least one group chosen from $C_1$-$C_4$ alkyl, ($C_1$-$C_4$)alkoxy($C_1$-$C_4$)alkyl, amino, di($C_1$-$C_4$)alkylamino, halogen, phenyl, carboxyl or tri($C_1$-$C_4$)alkylammonio($C_1$-$C_4$)alkyl groups.

Non-limiting mention may be made, by way of example, of:

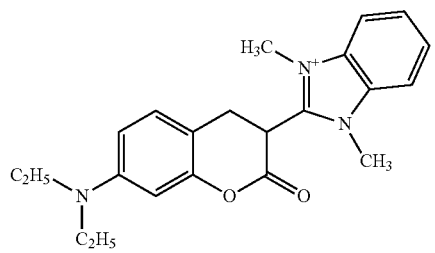 [SMILES: CCN(CC)c1ccc2c(c1)OC(=O)C(c1n(C)c3ccccc3[n+]1C)C2]

C.I. Basic Yellow 40
Xanthene derivatives, such as:

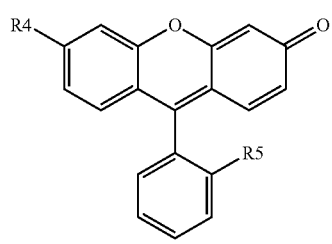

in which R4 and R5 are chosen from, which may be identical or different, hydrogen; a halogen; a $C_6$-$C_{30}$ aryl group; a hydroxyl group; a cyano group; a nitro group; a sulpho group; an amino group; an acylamino group; a di($C_1$-$C_6$)alkylamino group; a dihydroxy($C_1$-$C_6$)alkylamino group; a ($C_1$-$C_6$)alkylhydroxy($C_1$-$C_6$)alkylamino group; a ($C_1$-$C_6$)alkoxy group; a ($C_1$-$C_6$)alkoxycarbonyl group; a carboxy($C_1$-$C_6$)alkoxy group; a piperidinosulphonyl group; a pyrrolidino group; a ($C_1$-$C_6$)alkylhalo($C_1$-$C_6$)alkylamino group; a benzoyl($C_1$-$C_6$)alkyl group; a vinyl group; a formyl group; a $C_6$-$C_{30}$ aryl radical optionally substituted by at least one group chosen from a hydroxyl group, a linear, branched or cyclic $C_1$-$C_6$ alkoxy group or a linear, branched or cyclic alkyl group comprising from 1 to 22 carbon atoms, itself optionally being substituted by at least one hydroxyl, amino or $C_1$-$C_6$ alkoxy group; a linear, branched or cyclic alkyl radical comprising from 1 to 22 carbon atoms, for example from 1 to 6 carbon atoms, optionally substituted by at least one group chosen from hydroxyl, amino, linear, branched or cyclic $C_1$-$C_6$ alkoxy, optionally substituted aryl, carboxyl or sulpho groups or a halogen, it being possible for this alkyl radical to be interrupted by a heteroatom, such as nitrogen, sulfur and oxygen.

Rhodamines, such as:

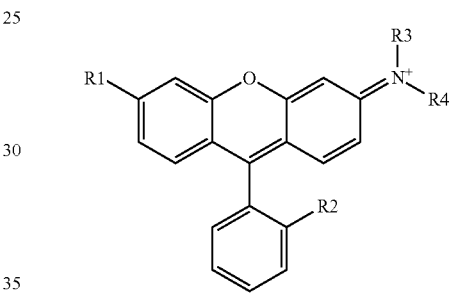

wherein R1, R2, R3 and R4 are as defined above. Non-limiting mention may be made, by way of example, of:

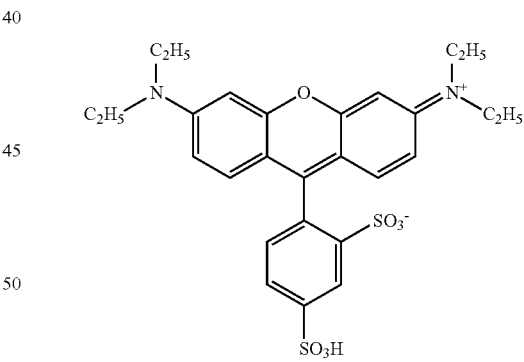

Sulphorhodamine B C.I. 45100 Acid Red 52
Thioxanthene derivatives, such as:

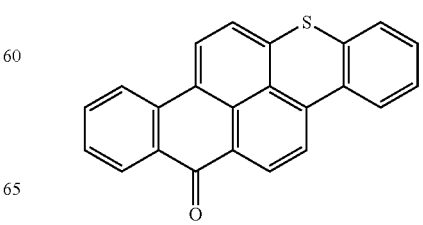

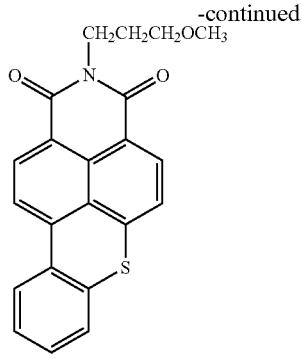

Samaron, Brilliant Yellow H6GL, C.I. 56235 Disperse Yellow 105

Naphtholactam derivatives, such as:

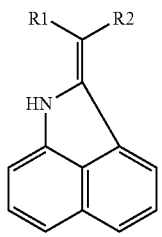

with $R_1$ and $R_2$ defined as above.

Non-limiting mention may be made, for example, of the following compound:

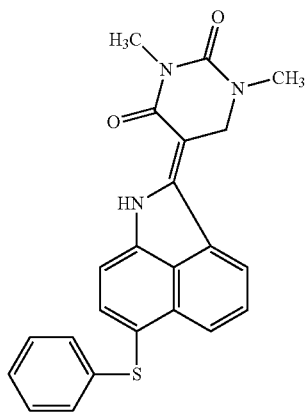 [SMILES: CN1C/C(=c2/[nH]c3ccc(Sc4ccccc4)c4cccc2c34)C(=O)N(C)C1=O]

Disperse Dye 28

Azalactone Derivatives:

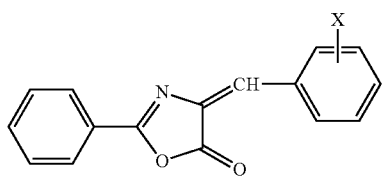

X having the same definition as R1 described above.

Non-limiting mention may be made, for example, of the following compound:

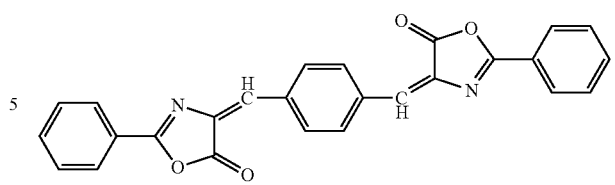

Methine derivatives, such as:

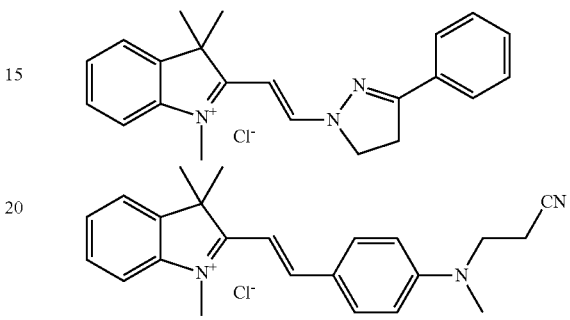

Oxazine and thiazine derivatives, such as:

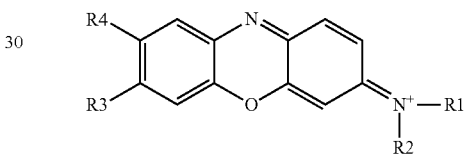

in which R1, R2, R3 and R4 are as defined above. Non-limiting mention may be made, by way of example, of:

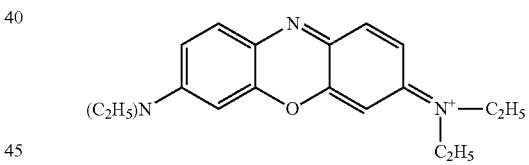

Basic Blue 3, C.I. 51004

1,4-Distyrylbenzene derivatives of formula:

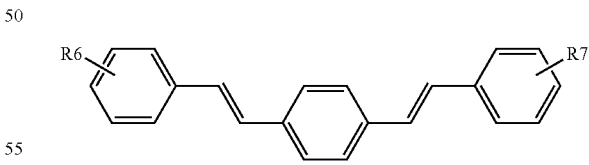

wherein R6 and R7 which may be identical or different, are chosen from hydrogen; a halogen; a $C_6$-$C_{30}$ aryl group; a hydroxyl group; a cyano group; a nitro group; a sulpho group; an amino group; an acylamino group; a di($C_1$-$C_6$) alkylamino group; a dihydroxy($C_1$-$C_6$)alkylamino group; a ($C_1$-$C_6$)alkylhydroxy($C_1$-$C_6$)alkylamino group; a ($C_1$-$C_6$) alkoxy group; a ($C_1$-$C_6$)alkoxycarbonyl group; a carboxy ($C_1$-$C_6$)alkoxy group; a piperidinosulphonyl group; a pyrrolidino group; a ($C_1$-$C_6$)alkylhalo($C_1$-$C_6$)alkylamino group; a benzoyl($C_1$-$C_6$)alkyl group; a vinyl group; a formyl group; a $C_6$-$C_{30}$ aryl radical optionally substituted by at least one group chosen from a hydroxyl group, a linear, branched or cyclic $C_1$-$C_6$ alkoxy group or a linear, branched or cyclic alkyl group comprising from 1 to 22 carbon atoms, itself optionally being substituted by at least one group chosen from hydroxyl, amino or $C_1$-$C_6$ alkoxy groups; a linear, branched or cyclic alkyl radical comprising from 1 to 22 carbon atoms, for example from 1 to 6 carbon atoms, optionally substituted by at least one group chosen from hydroxyl, amino, linear, branched or cyclic $C_1$-$C_6$ alkoxy, optionally substituted aryl, carboxyl or sulpho groups or a halogen, it being possible for this alkyl radical to be interrupted by a heteroatom, such as N, S or O.

4,4'-Distyrylbiphenyl derivatives of formula:

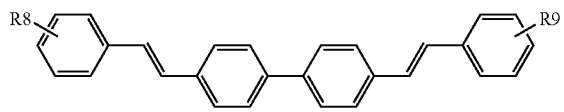

wherein R8 and R9 which may be identical or different, are chosen from hydrogen; a halogen; a $C_6$-$C_{30}$ aryl group; a hydroxyl group; a cyano group; a nitro group; a sulpho group; an amino group; an acylamino group; a di($C_1$-$C_6$)alkylamino group; a dihydroxy($C_1$-$C_6$)alkylamino group; a ($C_1$-$C_6$)alkylhydroxy($C_1$-$C_6$)alkylamino group; a ($C_1$-$C_6$)alkoxy group; a ($C_1$-$C_6$)alkoxycarbonyl group; a carboxy($C_1$-$C_6$)alkoxy group; a piperidinosulphonyl group; a pyrrolidino group; a ($C_1$-$C_6$)alkylhalo($C_1$-$C_6$)alkylamino group; a benzoyl($C_1$-$C_6$)alkyl group; a vinyl group; a formyl group; a $C_6$-$C_{30}$ aryl radical optionally substituted by at least one group chosen from a hydroxyl group, a linear, branched or cyclic $C_1$-$C_6$ alkoxy group or a linear, branched or cyclic alkyl group comprising from 1 to 22 carbon atoms, itself optionally being substituted by at least one group chosen from hydroxyl, amino or $C_1$-$C_6$ alkoxy groups; a linear, branched or cyclic alkyl radical comprising from 1 to 22 carbon atoms, for example from 1 to 6 carbon atoms, optionally substituted by at least one group chosen from hydroxyl, amino, linear, branched or cyclic $C_1$-$C_6$ alkoxy, optionally substituted aryl, carboxyl or sulpho groups or a halogen, it being possible for this alkyl radical to be interrupted by a heteroatom, such as nitrogen, sulfur or oxygen.

Triazinylaminostilbene derivatives of formula:

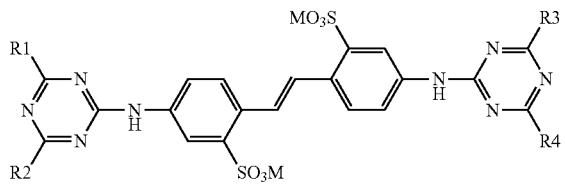

wherein R1, R2, R3 and R4 which may be identical or different, are chosen from hydrogen; a halogen; a $C_6$-$C_{30}$ aryl group; a hydroxyl group; a cyano group; a nitro group; a sulpho group; an amino group; an acylamino group; a di($C_1$-$C_6$)alkylamino group; a dihydroxy($C_1$-$C_6$)alkylamino group; a ($C_1$-$C_6$)alkylhydroxy($C_1$-$C_6$)alkylamino group; a ($C_1$-$C_6$)alkoxy group; a ($C_1$-$C_6$)alkoxycarbonyl group; a carboxy($C_1$-$C_6$)alkoxy group; a piperidinosulphonyl group; a pyrrolidino group; a ($C_1$-$C_6$)alkylhalo($C_1$-$C_6$)alkylamino group; a benzoyl($C_1$-$C_6$)alkyl group; a vinyl group; a formyl group; a $C_6$-$C_{30}$ aryl radical optionally substituted by at least one group chosen from a hydroxyl group, a linear, branched or cyclic $C_1$-$C_6$ alkoxy group or a linear, branched or cyclic alkyl group comprising from 1 to 22 carbon atoms, itself optionally being substituted by at least one group chosen from hydroxyl, amino or $C_1$-$C_6$ alkoxy groups; a linear, branched or cyclic alkyl radical comprising from 1 to 22 carbon atoms, for example from 1 to 6 carbon atoms, optionally substituted by at least one group chosen from hydroxyl, amino, linear, branched or cyclic $C_1$-$C_6$ alkoxy, optionally substituted aryl, carboxyl or sulpho groups or a halogen, it being possible for this alkyl radical to be interrupted by a heteroatom, such as nitrogen, sulfur and oxygen;

and M is a monovalent or divalent cation resulting from the family of alkali metals or alkaline-earth metals, such as, for example, sodium, potassium and calcium ions.

Stilbazolium derivatives of formula:

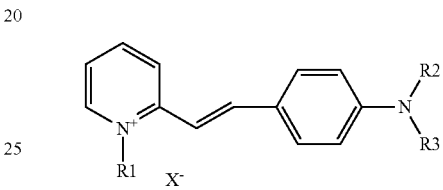

wherein R1, R2 and R3 which may be identical or different, are chosen from hydrogen; a halogen; a $C_6$-$C_{30}$ aryl group; a hydroxyl group; a cyano group; a nitro group; a sulpho group; an amino group; an acylamino group; a di($C_1$-$C_6$)alkylamino group; a dihydroxy($C_1$-$C_6$)alkylamino group; a ($C_1$-$C_6$)alkylhydroxy($C_1$-$C_6$)alkylamino group; a ($C_1$-$C_6$)alkoxy group; a ($C_1$-$C_6$)alkoxycarbonyl group; a carboxy($C_1$-$C_6$)alkoxy group; a piperidinosulphonyl group; a pyrrolidino group; a ($C_1$-$C_6$)alkylhalo($C_1$-$C_6$)alkylamino group; a benzoyl($C_1$-$C_6$)alkyl group; a vinyl group; a formyl group; a $C_6$-$C_{30}$ aryl radical optionally substituted by at least one group chosen from a hydroxyl group, a linear, branched or cyclic $C_1$-$C_6$ alkoxy group or a linear, branched or cyclic alkyl group comprising from 1 to 22 carbon atoms, itself optionally being substituted by at least one group chosen from hydroxyl, amino or $C_1$-$C_6$ alkoxy groups; a linear, branched or cyclic alkyl radical comprising from 1 to 22 carbon atoms, for example from 1 to 6 carbon atoms, optionally substituted by at least one group chosen from hydroxyl, amino, linear, branched or cyclic $C_1$-$C_6$ alkoxy, optionally substituted aryl, carboxyl or sulpho groups or a halogen it being possible for this alkyl radical to be interrupted by a heteroatom, such as nitrogen, sulfur and oxygen;

two of the R2 and R3 substituents can form, with the carbon atoms to which they are attached, a $C_6$-$C_{30}$ aromatic ring or a heterocyclic ring comprising, in total, from 5 to 30 ring members and from 1 to 5 heteroatoms; this ring being fused or non-fused, this ring and the possible fused ring being unsubstituted or substituted by at least one group chosen from $C_1$-$C_4$ alkyl, ($C_1$-$C_4$)alkoxy($C_1$-$C_4$)alkyl, amino, di($C_1$-$C_4$)alkylamino, halogen, phenyl, carboxyl or tri($C_1$-$C_4$)alkylammonio($C_1$-$C_4$)alkyl groups; and $X^-$ is an organic or inorganic anion. Non-limiting mention may be made, for example, for $X^-$, of chloride, bromide, iodide, methosulphate, ethosulphate, mesylate, tosylate or acetate ions or simple organic acid salts, such as lactates, oleates, benzoates, perchlorates or triflates.

Stilbazolium dimers of formulae:

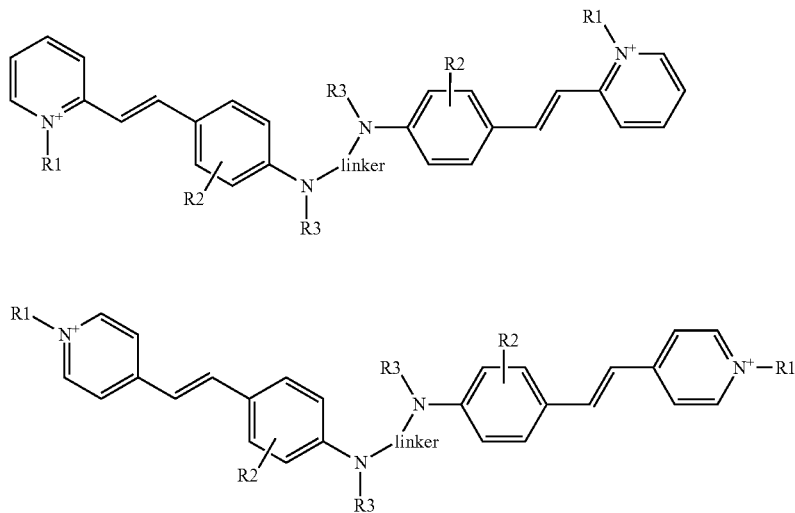

wherein R1, R2 and R3 which may be identical or different, are chosen from hydrogen; a halogen; a $C_6$-$C_{30}$ aryl group; a hydroxyl group; a cyano group; a nitro group; a sulpho group; an amino group; an acylamino group; a di($C_1$-$C_6$)alkylamino group; a dihydroxy($C_1$-$C_6$)alkylamino group; a ($C_1$-$C_6$)alkylhydroxy($C_1$-$C_6$)alkylamino group; a ($C_1$-$C_6$)alkoxy group; a ($C_1$-$C_6$)alkoxycarbonyl group; a carboxy($C_1$-$C_6$)alkoxy group; a piperidinosulphonyl group; a pyrrolidino group; a ($C_1$-$C_6$)alkylhalo($C_1$-$C_6$)alkylamino group; a benzoyl($C_1$-$C_6$)alkyl group; a vinyl group; a formyl group; a $C_6$-$C_{30}$ aryl radical optionally substituted by at least one group chosen from a hydroxyl group, a linear, branched or cyclic $C_1$-$C_6$ alkoxy group or a linear, branched or cyclic alkyl group comprising from 1 to 22 carbon atoms, itself optionally being substituted by at least one group chosen from hydroxyl, amino or $C_1$-$C_6$ alkoxy groups; a linear, branched or cyclic alkyl radical comprising from 1 to 22 carbon atoms, for example from 1 to 6 carbon atoms, optionally substituted by at least one group chosen from hydroxyl, amino, linear, branched or cyclic $C_1$-$C_6$ alkoxy, optionally substituted aryl, carboxyl or sulpha groups or a halogen, it being possible for this alkyl radical to be interrupted by a heteroatom, such as nitrogen, sulfur and oxygen.

The following stilbazolium trimers and tetramers:

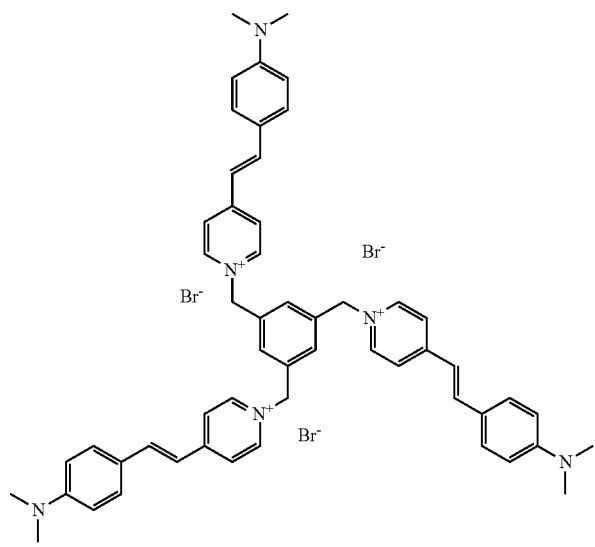

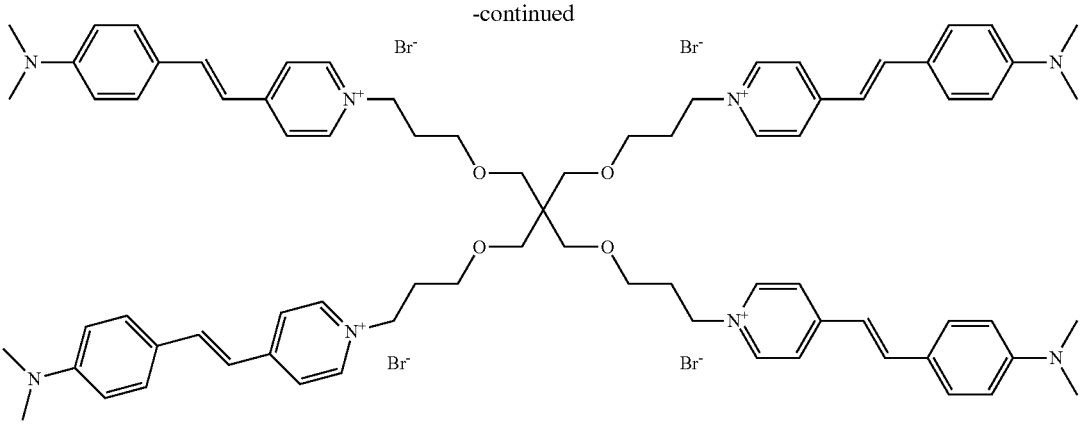

Bis(benzoxazole) derivatives of formula:

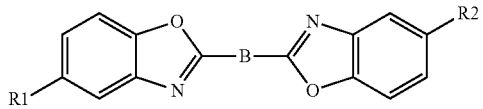

wherein R1 and R2 which may be identical or different, are chosen from hydrogen; a halogen; a $C_6$-$C_{30}$ aryl group; a hydroxyl group; a cyano group; a nitro group; a sulpho group; an amino group; an acylamino group; a di($C_1$-$C_6$)alkylamino group; a dihydroxy($C_1$-$C_6$)alkylamino group; a ($C_1$-$C_6$)alkylhydroxy($C_1$-$C_6$)alkylamino group; a ($C_1$-$C_6$) alkoxy group; a ($C_1$-$C_6$)alkoxycarbonyl group; a carboxy ($C_1$-$C_6$)alkoxy group; a piperidinosulphonyl group; a pyrrolidino group; a ($C_1$-$C_6$)alkylhalo($C_1$-$C_6$)alkylamino group; a benzoyl($C_1$-$C_6$)alkyl group; a vinyl group; a formyl group; a $C_6$-$C_{30}$ aryl radical optionally substituted by at least one group chosen from a hydroxyl group, a linear, branched or cyclic $C_1$-$C_6$ alkoxy group or a linear, branched or cyclic alkyl group comprising from 1 to 22 carbon atoms, itself optionally being substituted by at least one group chosen from hydroxyl, amino or $C_1$-$C_6$ alkoxy groups; a linear, branched or cyclic alkyl radical comprising from 1 to 22 carbon atoms, for example from 1 to 6 carbon atoms, optionally substituted by at least one group chosen from hydroxyl, amino, linear, branched or cyclic $C_1$-$C_6$ alkoxy, optionally substituted aryl, carboxyl or sulpho groups or a halogen, it being possible for this alkyl radical to be interrupted by a heteroatom, such as nitrogen, sulfur and oxygen; and B is chosen from:

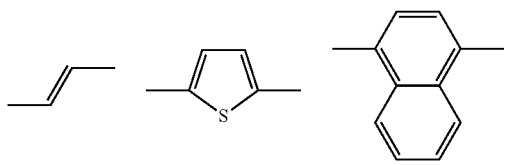

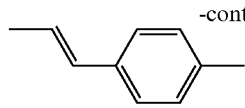

Cationic or non-cationic bis(benzimidazoles);
Anionic or non-anionic 1,3-diphenyl-2-pyrazolines, for example:

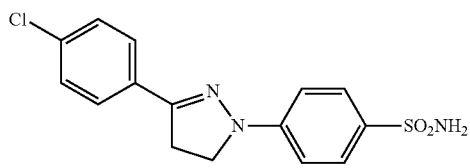 [SMILES: NS(=O)(=O)c1ccc(N2CCC(c3ccc(Cl)cc3)=N2)cc1]

Diketopyrrolopyrroles of formula:

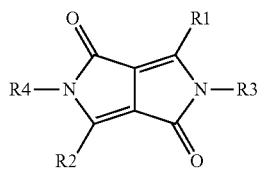

wherein R1, R2, R3 and R4 which may be identical or different, are chosen from hydrogen; a halogen; a $C_6$-$C_{30}$ aryl group; a hydroxyl group; a cyano group; a nitro group; a sulpho group; an amino group; an acylamino group; a di($C_1$-$C_6$)alkylamino group; a dihydroxy($C_1$-$C_6$)alkylamino group; a ($C_1$-$C_6$)alkylhydroxy($C_1$-$C_6$)alkylamino group; a ($C_1$-$C_6$)alkoxy group; a ($C_1$-$C_6$)alkoxycarbonyl group; a carboxy($C_1$-$C_6$)alkoxy group; a piperidinosulphonyl group; a pyrrolidino group; a ($C_1$-$C_6$)alkylhalo($C_1$-$C_6$)alkylamino group; a benzoyl($C_1$-$C_6$)alkyl group; a vinyl group; a formyl group; a $C_6$-$C_{30}$ aryl radical optionally substituted by at least one group chosen from a hydroxyl group, a linear, branched or cyclic $C_1$-$C_6$ alkoxy group or a linear, branched or cyclic alkyl group comprising from 1 to 22 carbon atoms, itself optionally being substituted by at least one group chosen from hydroxyl, amino or $C_1$-$C_6$ alkoxy group; a linear, branched or cyclic alkyl radical comprising from 1 to 22 carbon atoms, for example from 1 to 6 carbon atoms, optionally substituted by at least one group chosen from hydroxyl, amino, linear, branched or cyclic $C_1$-$C_6$ alkoxy, optionally substituted aryl, carboxyl or sulpho groups or a halogen, it being possible for this alkyl radical to be interrupted by a heteroatom, such as nitrogen, sulfur and oxygen.

Non-limiting mention may be made, for example, of the following compound:

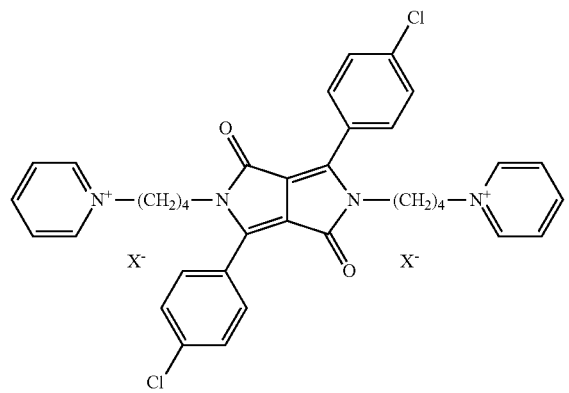

in which $X^-$ is an anion defined as above.
Dicyanopyrazine derivatives of formulae:

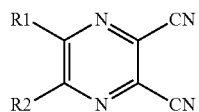 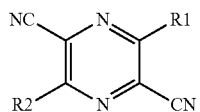

wherein R1 and R2 which may be identical or different, are chosen from hydrogen; a halogen; a $C_6$-$C_{30}$ aryl group; a hydroxyl group; a cyano group; a nitro group; a sulpho group; an amino group; an acylamino group; a di($C_1$-$C_6$)alkylamino group; a dihydroxy($C_1$-$C_6$)alkylamino group; a ($C_1$-$C_6$)alkylhydroxy($C_1$-$C_6$)alkylamino group; a ($C_1$-$C_6$) alkoxy group; a ($C_1$-$C_6$)alkoxycarbonyl group; a carboxy($C_1$-$C_6$)alkoxy group; a piperidinosulphonyl group; a pyrrolidino group; a ($C_1$-$C_6$)alkylhalo($C_1$-$C_6$)alkylamino group; a benzoyl($C_1$-$C_6$)alkyl group; a vinyl group; a formyl group; a $C_5$-$C_{30}$ aryl radical optionally substituted by at least one group chosen from a hydroxyl group, a linear, branched or cyclic $C_1$-$C_6$ alkoxy group or a linear, branched or cyclic alkyl group comprising from 1 to 22 carbon atoms, itself optionally being substituted by at least one group chosen from a hydroxyl, amino or $C_1$-$C_6$ alkoxy group; a linear, branched or cyclic alkyl radical comprising from 1 to 22 carbon atoms, for example from 1 to 6 carbon atoms, optionally substituted by at least one group chosen from hydroxyl, amino, linear, branched or cyclic $C_1$-$C_6$ alkoxy, optionally substituted aryl, carboxyl or sulpho groups or a halogen, it being possible for this alkyl radical to be interrupted by a heteroatom, such as nitrogen, sulfur and oxygen; and two of the R1 and R2 substituents can form, with the carbon atoms to which they are attached, a $C_6$-$C_{30}$ aromatic or non-aromatic ring or a heterocyclic ring comprising, in total, from 5 to 30 ring members and from 1 to 5 heteroatoms; these rings being fused or non-fused and inserting or not inserting a carbonyl group and being unsubstituted or substituted by at least one group chosen from $C_1$-$C_4$ alkyl, ($C_1$-$C_4$)alkoxy($C_1$-$C_4$)alkyl, amino, di($C_1$-$C_4$)alkylamino, halogen, phenyl, carboxyl or tri($C_1$-$C_4$)alkylammonio($C_1$-$C_4$)alkyl groups.

Non-limiting mention may be made of the compounds in the following publication: "Selective topochemical photoreaction of crystallized 2,3-(-phenyletheny)-4,5-dicyanopyrazine" by Kim, Jae Hong; Matsuoka Masaru, Chem. Lett. (1999), (2), 143-144.

Non-limiting mention may be made of:

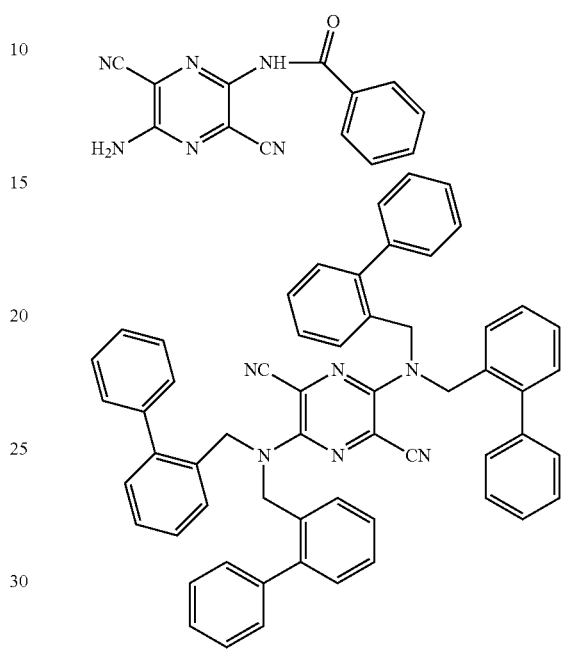

The colored entity present in the composition of the present disclosure may be a pigment.

As used herein, the term "pigment" means any organic and/or inorganic entity having a solubility in water of less than 0.01% at 20° C., for example of less than 0.0001%, and exhibiting an absorption ranging from 350 to 750 nm, for instance an absorption with a maximum.

The pigments that can be used are chosen from organic and/or inorganic pigments known from the art, for example those which are described in Kirk-Othmer's Encyclopedia of Chemical Technology and in Ullmann's Encyclopedia of Industrial Chemistry.

These pigments may be in the form of a powder or of a pigment paste. They can be coated or uncoated.

The pigments can, for example, be chosen from inorganic pigments, organic pigments, lakes, special-effect pigments, such as pearlescent agents or glitter, and mixtures thereof.

The pigment can be an inorganic pigment. As used herein, the term "inorganic pigment" means any pigment which corresponds to the definition of Ullmann's Encyclopedia in the "Inorganic Pigment" chapter. Non-limiting mention may be made, among inorganic pigments used in the present disclosure, of titanium dioxide, which is or is not surface-treated, zirconium or cerium oxides, iron or chromium oxides, manganese violet, ultramarine blue, chromium hydrate and ferric blue. For instance, inorganic pigments include but are not limited to: $Ta_2O_5$, $Ti_3O_5$, $Ti_2O_3$, $TiO$, $ZrO_2$ as a mixture with $TiO_2$, $ZrO_2$, $Nb_2O_5$, $CeO_2$, $ZnS$.

The pigment that is not surface-treated, subsequently referred to as "pigment," may be an organic pigment. As included herein, the term "organic pigment" means any pigment which corresponds to the definition of Ullmann's Encyclopedia in the "Organic Pigment" chapter. The organic pigment can be chosen from nitroso, nitro, azo, xanthene, quinoline, anthraquinone or phthalocyanine compounds, compounds of metal complex type, or isoindolinone, isoindoline, quinacridone, perinone, perylene, diketopyrrolopyrrole, thioindigo, dioxazine, triphenylmethane or quinophthalone compounds.

In at least one embodiment, white or colored organic pigments can be chosen from carmine, carbon black, aniline black, azo yellow, quinacridone, phthalocyanine blue, sorghum red, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, or the pigments obtained by oxidative polymerization of indole or phenol derivatives, disclosed for example in, French Patent No. FR 2,679,771.

Non-limiting mention may also be made, for example, of pigment pastes formed of organic pigment, such as the products sold by Hoechst under the name:

Cosmenyl Yellow IOG: Pigment Yellow 3 (CI 11710);
Cosmenyl Yellow G: Pigment Yellow 1 (CI 11680);
Cosmenyl Orange GR: Pigment Orange 43 (CI 71105);
Cosmenyl Red R: Pigment Red 4 (CI 12085);
Cosmenyl Carmine FB: Pigment Red 5 (CI 12490);
Cosmenyl Violet RL: Pigment Violet 23 (CI 51319);
Cosmenyl Blue A2R: Pigment Blue 15.1 (CI 74160)
Cosmenyl Green GG: Pigment Green 7 (CI 74260);
Cosmenyl Black R: Pigment Black 7 (CI 77266).

The pigments in accordance with the present disclosure can also be in the form of composite pigments, such as those described in European Patent No. 1 184 426. These composite pigments can be composed of particles comprising an inorganic core, at least one binder, which provides for the attachment of the organic pigments to the core, and at least one organic pigment which at least partially covers the core.

The organic pigment can also be a lake. As included herein, the term "lake" means dyes adsorbed onto insoluble particles, the combination thus obtained remaining insoluble during use.

The inorganic substrates onto which the dyes are adsorbed are, for example, alumina, silica, calcium sodium borosilicate, calcium aluminum borosilicate and aluminum.

Non-limiting mention may be made, among the dyes, of cochineal carmine. Non-limiting mention may also be made of the dyes known under the following names: D & C Red 21 (CI 45 380), D & C Orange 5 (CI 45 370), D & C Red 27 (CI 45 410), D & C Orange 10 (CI 45 425), D & C Red 3 (CI 45 430), D & C Red 4 (CI 15 510), D & C Red 33 (CI 17 200), D & C Yellow 5 (CI 19 140), D & C Yellow 6 (CI 15 985), D & C Green (CI 61 570), D & C Yellow 1 O (CI 77 002), D & C Green 3 (CI 42 053), D & C Blue 1 (CI 42 090).

Non-limiting mention may be made, as examples of lakes, of the product known under the following name: D & C Red 7 (CI 15 850:1).

The pigment can also be a special-effect pigment. As used herein, the term "special effect pigments" means pigments which generally create a colored appearance (characterized by a certain hue, a certain vividness and a certain lightness) which is not uniform and which changes as a function of the conditions of observation (light, temperature, angles of observation, etc.). They thereby contrast with white or colored pigments, which provide a conventional opaque, semitransparent or transparent uniform color.

There are several types of special-effect pigments, those with a low refractive index, such as fluorescent, photochromic or thermochromic pigments, and those with a higher refractive index, such as pearlescent agents or glitter.

Non-limiting mention may be made, as examples of special effect pigments, of white pearlescent pigments, such as mica covered with titanium dioxide or with bismuth oxychloride, colored pearlescent pigments, such as mica covered with titanium dioxide and with iron oxides, mica covered with titanium dioxide and for example with ferric blue or with chromium oxide or mica covered with titanium dioxide and with an organic pigment as disclosed herein, and pearlescent pigments based on bismuth oxychloride. Non-limiting mention may be made, as pearlescent pigments, of the following pearlescent agents: Cellini sold by Engelhard (mica-$TiO_2$-lake), Prestige sold by Eckart (mica-$TiO_2$), Prestige Bronze sold by Eckart (mica-$Fe_2O_3$) or Colorona sold by Merck (mica-$TiO_2$—$Fe_2O_3$).

In addition to pearlescent agents on a mica support, it is possible to envisage multilayer pigments based on synthetic substrates, such as alumina, silica, calcium sodium borosilicate, calcium aluminum borosilicate and aluminum.

Non-limiting mention may also be made of pigments with an interference effect which are not attached to a substrate, such as liquid crystals (Helicones HC from Wacker) and interference holographic glitter (Geometric Pigment or Spectra fix from Spectratek). Special-effect pigments also may comprise fluorescent pigments, whether substances which are fluorescent in daylight or which produce ultraviolet fluorescence, phosphorescent pigments, photochromic pigments, thermochromic pigments and quantum dots, for example sold by Quantum Dots Corporation.

Quantum dots are luminescent semiconductor nanoparticles capable of emitting, under light excitation, radiation exhibiting a wavelength ranging from 400 nm to 700 nm. These nanoparticles are known from the literature. They can be synthesized according to the processes described, for example, in U.S. Pat. No. 6,225,198 or U.S. Pat. No. 5,990,479, in the publications which are cited therein and in the following publications: Dabboussi B. O. et al., "(CdSe) ZnS core-shell quantum dots: synthesis and characterisation of a size series of highly luminescent nanocrystallites," Journal of Physical Chemistry B, vol. 101, 1997, pp. 9463-9475, and Peng, Xiaogang et al., "Epitaxial growth of highly luminescent CdSe/CdS core/shell nanocrystals with photostability and electronic accessibility," Journal of the American Chemical Society, vol. 119, No. 30, pp. 7019-7029.

The variety of the pigments in the present disclosure make it possible to obtain a rich palette of colors as well as specific optical effects, such as interference, metallic effects.

In at least one embodiment, the pigments are colored pigments. As used herein, the term "colored pigment" means pigments other than white pigments.

The size of the pigment used in the cosmetic composition according to the present disclosure generally ranges from 10 nm to 200 µm, for example ranging from 20 nm to 80 µm or ranging from 30 nm to 50 µm.

The pigments can be dispersed in the product by virtue of a dispersant.

The dispersant serves to protect the dispersed particles from the agglomeration or flocculation thereof. This dispersant can be a surfactant, an oligomer, a polymer or a mixture of several of them bearing at least one functionality having a strong affinity for the surface of the particles to be dispersed. For example, they can become attached physically or chemically to the surface of the pigments. These dispersants additionally exhibit at least one functional group compatible with or soluble in the continuous medium. Mention may be made, for example, of esters of 12-hydroxystearic acid and of $C_8$ to $C_{20}$ fatty acid and of polyol, such as glycerol or diglycerol, such as the stearate of poly(12-hydroxy-stearic acid) with a molecular weight of 750 g/mol, such as that sold under the name of Solsperse 21 000 by Avecia, polyglyceryl-2 dipolyhydroxystearate (CTFA name), sold under the reference Dehymyls PGPH by Henkel, or else polyhydroxystearic acid, such as that sold under the reference Arlacel P100 by Uniqema, and mixtures thereof.

Mention may be made, as other dispersants which can be used in the compositions of the present disclosure, of the quaternary ammonium derivatives of polycondensed fatty acids, such as Solsperse 17 000, sold by Avecia, or polydimethylsiloxane/oxypropylene mixtures, such as those sold by Dow Corning under the references DC2-5185, DC2-5225 C.

The polydihydroxystearic acid and the esters of 12 hydroxystearic acid may be intended for a hydrocarbon-based or fluorinated medium, while the oxyethylene/oxypropylene polydimethylsiloxane mixtures are may be intended for a silicone-based medium.

The pigments used in the cosmetic composition in the present disclosure can be surface-treated with an organic agent.

Thus, the pre-surface-treated pigments that may be used according to the present disclosure are pigments or fillers which have been completely or partially subjected to a surface treatment of chemical, electronic, electrochemical, mechanochemical or mechanical nature with an organic agent, disclosed, for example in Cosmetics and Toiletries, February 1990, Vol. 105, pp. 53-64, before being dispersed in the composition in accordance with the present disclosure. These organic agents can, for example, be chosen from amino acids; waxes, for example carnauba wax and beeswax; fatty acids, fatty alcohols and derivatives thereof, such as stearic acid, hydroxystearic acid, stearyl alcohol, hydroxystearyl alcohol, lauric acid and derivatives thereof; anionic surfactants; lecithins; sodium, potassium, magnesium, iron, titanium, zinc or aluminum salts of fatty acids, for example aluminum stearate or laurate; metal alkoxides; polysaccharides, for example chitosan, cellulose and derivatives thereof; polyethylene; (meth)acrylic polymers, for example polymethyl methacrylates; polymers and copolymers comprising acrylate units; proteins; alkanolamines; silicone-based compounds, for example silicones, polydimethylsiloxanes, alkoxysilanes, alkylsilanes or siloxysilicates; fluorinated organic compounds, for example perfluoroalkyl ethers; or fluorosilicone compounds.

The surface-treated pigments that may be used in the cosmetic composition according to the present disclosure may also have been treated with a mixture of these compounds and/or have undergone several surface treatments.

The surface-treated pigments of use in the present disclosure can be prepared according to surface-treatment techniques well known to a person skilled in the art or found as such commercially.

In at least one embodiment, the surface-treated pigments are covered with an organic layer.

The organic agent with which the pigments may be treated can be deposited on the pigments by evaporation of solvent, chemical reaction between the molecules of the surface agent or creation of a covalent bond between the surface agent and the pigments.

The surface treatment can thus be carried out, for example, by chemical reaction of a surface agent with the surface of the pigments and creation of a covalent bond between the surface agent and the pigments or fillers. This method is disclosed for example in U.S. Pat. No. 4,578,266.

In at least one embodiment, use may be made of an organic agent covalently bonded to the pigments.

The agent for the surface treatment can be present in an amount ranging from 0.1 to 50% by weight, for example ranging from 0.5 to 30% by weight or ranging from 1 to 10% by weight of the total weight of the surface-treated pigments.

By way of non-limiting example, the surface treatment of the pigments can be chosen from the following treatments:

a PEG-silicone treatment, such as the AQ surface treatment marketed by LCW;

a chitosan treatment, such as the CTS surface treatment marketed by LCW;

a triethoxycaprylylsilane treatment, such as the AS surface treatment marketed by LCW;

a methicone treatment, such as the SI surface treatment marketed by LCW;

a dimethicone treatment, such as the Covasil 3.05 surface treatment marketed by LCW;

a dimethicone/trimethylsiloxysilicate treatment, such as the Covasil 4.05 surface treatment marketed by LOW;

a lauroyl lysine treatment, such as the LL surface treatment marketed by LCW;

a lauroyl lysine dimethicone treatment, such as the LL/SI surface treatment marketed by LCW;

a magnesium myristate treatment, such as the MM surface treatment marketed by LCW;

an aluminum dimyristate treatment, such as the MI surface treatment marketed by Miyoshi;

a perfluoropolymethylisopropyl ether treatment, such as the FHC surface treatment marketed by LCW;

an isostearyl sebacate treatment, such as the HS surface treatment marketed by Miyoshi;

a disodium stearoyl glutamate treatment, such as the NAI surface treatment marketed by Miyoshi;

a dimethicone/disodium stearoyl glutamate treatment, such as the SA/NAI surface treatment marketed by Miyoshi;

a perfluoroalkyl phosphate treatment, such as the PF surface treatment marketed by Daito;

an acrylate/dimethicone copolymer and perfluoalkyl phosphate treatment, such as the FSA surface treatment marketed by Daito;

a polymethylhydrosiloxane/perfluoalkyl phosphate treatment, such as the FS01 surface treatment marketed by Daito;

a lauryl lysine/aluminum tristearate treatment, such as the LL-StAI surface treatment marketed by Daito;

an octyltriethylsilane treatment, such as the OTS surface treatment marketed by Daito;

an octyltriethylsilane/perfluoalkyl phosphate treatment, such as the FOTS surface treatment marketed by Daito;

an acrylate/dimethicone copolymer treatment, such as the ASC surface treatment marketed by Daito;

an isopropyl titanium triisostearate treatment, such as the ITT surface treatment marketed by Daito;

a microcrystalline cellulose and carboxymethyl cellulose treatment, such as the AC surface treatment marketed by Daito;

a cellulose treatment, such as the C2 surface treatment marketed by Daito;

an acrylate copolymer treatment, such as the APD surface treatment marketed by Daito; and a perfluoalkyl phosphate/isopropyl titanium triisostearate treatment, such as the PF+ITT surface treatment marketed by Daito.

The composition in accordance with the present disclosure can furthermore comprise at least one pigment which is not surface treated.

Non-limiting mention maybe made, among coloring entities, of dye precursors, such as oxidation bases and couplers. Non-limiting mention may also be made, among oxidation bases conventionally used in oxidation dyeing, of para-phenylenediamines, bisphenylalkylenediamines, para-aminophenols, ortho-aminophenols and heterocyclic bases. Non-limiting mention may further be made, among couplers, of meta-phenylenediamines, meta-aminophenols, meta-diphenols, naphthols and heterocyclic couplers, such as, for example, indole derivatives, indoline derivatives, pyridine derivatives, indazole derivatives, pyrazolo[1,5-b]-1,2,4-triazole derivatives, pyrazolo[3,2-c]-1,2,4-triazole derivatives, benzimidazole derivatives, benzothiazole derivatives, benzoxazole derivatives, 1,3-benzodioxole derivatives and pyrazolones, and addition salts thereof with an acid The at least one colored or coloring entity in the composition can be present in an amount ranging from 0.01 to 50%, for example ranging from 0.5 to 20%.

In at least one embodiment, the at least one colored entity is a pigment.

In the present disclosure, the composition used may also comprise at least one adjuvant.

This or these adjuvant(s) can be chosen from organomodified or non-organomodified silicones other than the polymers of the present disclosure, such as aminosilicones, fixative or non-fixative cationic, anionic, amphoteric or non-ionic polymers, peptides and derivatives thereof, protein hydrolysates, waxes, swelling agents and penetrants such as dimethylisosorbitol, urea and derivatives thereof, anionic, cationic, non-ionic, amphoteric or zwitterionic surfactants, agents for combating hair loss, anti-dandruff agents, natural or synthetic associative or non-associative thickeners, suspension agents, sequestering agents, sunscreens, vitamins or provitamins, fatty acids, fatty alcohols, fatty esters, mineral, plant or synthetic oils, and also fragrances and preservatives and mixtures thereof.

The at least one adjuvant can be present in an amount ranging from 0.01 to 30%, for example ranging from 0.1 to 10%, by weight of the total weight of the cosmetic composition.

The composition according to the present disclosure may comprise at least one cosmetically acceptable solvent is chosen from water, $C_1$-$C_6$ alcohols, such as alkanols for example ethanol, propanol and isopropanol, polyols such as propylene glycol, glycerol and pentanediol, benzyl alcohol, polyol ethers, $C_2$-$C_6$ esters, N-methylpyrrolidone (NMP), $C_3$-$C_6$ ketones, and silicone oils.

If the composition is aqueous, its pH can range from 2 to 13, for example from 4 to 10.

Adjustment of the pH of the composition may be obtained using at least one alkaline agent such as, ammonium hydroxide, monoethanolamine, diethanolamine, triethanolamine, 1,3-propanediamine, an alkali metal carbonate or bicarbonate or ammonium carbonate or bicarbonate, an organic carbonate such as guanidine carbonate, an alkali metal hydroxide, or else using at least one acidifying agent such as, for example, hydrochloric acid, acetic acid, lactic acid, oxalic acid or boric acid.

In at least one embodiment, the composition applied according to the process according to the present disclosure is anhydrous, that is to say containing substantially no water, for example less than 1% water.

In at least one embodiment, the solvent used is ethanol or a silicone oil.

The composition used in the process according to the present disclosure may be in the form of a thick or thin lotion, a cream or a gel, a wax or an aerosol mousse.

The compositions may be contained in devices such as a pump dispenser or an aerosol spray.

Process Steps

The composition can be applied to wet hair fibers. This application may or may not be followed by a rinsing step.

The composition can be applied to the hair fibers in an amount ranging from 0.05 to 0.3 g, for example 0.1 to 0.2 g of composition per gram of dry hair fiber.

After applying the composition, and before heating the hair fibers, the composition disclosed herein may be left on for a period of time ranging from 30 seconds to 60 minutes, for example from 5 to 45 minutes.

As disclosed herein, the process comprises, after applying the composition, heating the hair fibers at a temperature ranging from 50 to 280° C. For example, the hair fibers are heated at a temperature ranging from 60° C. to 250° C., for example ranging from 120° C. to 220° C.

In at least one embodiment, the heating is achieved using irons.

As used herein, the term "irons" means a device for heating hair fibers that brings said fibers and the heating device into contact.

By way of non-limiting example, the irons that can be used include curling irons, straightening irons or waving irons.

By way of example of irons that can be used in the process according to the present disclosure, further non-limiting mention may be made of all types of flat or round irons and, such as those disclosed in U.S. Pat. Nos. 4,103,145; 4,308,878; 5,983,903; 5,957,140; 5,494,058; and 5,046,516.

In flat irons, the end of the iron that comes into contact with the hair has two planar surfaces. These two planar surfaces may be metallic. They may be smooth or notched.

The application of the iron may be carried out by successive separate touches of a few seconds, or by gradual movement or sliding along the locks.

For example, in at least one embodiment, the application of the iron in the process according to the present disclosure is carried out by continuous movement from the root to the tip, in at least one pass.

The process according to the present disclosure may also optionally comprise completely or partially pre-drying the hair fibers before heating, so as to avoid large releases of steam which could burn the hands of the hairstylist and the scalp of the individual being treated. This pre-drying step may be carried out, for example, using a hairdryer, or a hood at a temperature below 50° C., or else by natural drying.

The heating may be simultaneous with the application of the composition according to the present disclosure.

In at least one embodiment, the heating follows the application of the composition according to the present disclosure.

The disclosed process may be carried out by using a device comprising a heat source combined with a reservoir of the cosmetic composition comprising the polymer. By way of example, such a conditioning and application device may comprise:

a heated or unheated reservoir;

a composition containing at least one polymer according to the present disclosure;

an application device;

a heating source positioned on both sides of the application device that makes it possible to heat the cosmetic composition to the desired temperature at the same time as, or after, it is applied. The heating source may thus act as an applicator.

In at least one embodiment of the present disclosure, the treatment according to the present disclosure is combined with an existing fiber treatment.

Thus, it is possible to apply a permanent wave or oxidation dyeing or bleaching or shampooing or styling product or alkaline straightening and then carry out the process disclosed herein. Thus, the durability of the first treatment is improved.

In at least one embodiment, the process comprises performing the process according to the present disclosure before performing any existing fiber treatments, which are known for damaging the keratin fiber (permanent wave, oxidation dyeing, bleaching, straightening). In this way, the fiber is also protected during the treatment.

The process of the present disclosure can make it possible to easily confer a thermoreversible shape to the fibers and may improve their sheen and their feel in a long-lasting manner.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

EXAMPLES

The process for treating hair fibers according to the present disclosure was carried out with the following compositions. The percentages used are given by weight relative to the total weight of the composition.

Example 1

| | |
|---|---|
| POLYUREADIMETHICONE (WACKER-BELSIL UD 80) | 2% |
| CYCLOPENTASILOXANE DOW CORNING 245 FLUID | 43% |
| ETHANOL | 55% |

1 g of this composition was applied to a 2.7 g lock of brown hair that had previously been shampooed. The lock was dried with a hairdryer for 30 min. The lock was heated by being wound around a curling iron at 200° C. to obtain a "ringlet."

After treatment, the hair was soft and shiny. The same lock was then straightened with a flat iron and then recurled with the curling iron. The curl obtained was identical to that from the first step (thermoreversibility).

Example 2

| | |
|---|---|
| POLYUREADIMETHICONE (WACKER-BELSIL UD 80) | 2% |
| CYCLOHEXASILOXANE DOW CORNING 246 FLUID | 41% |
| ETHANOL | 55% |
| Candurin Blue Shimmer pearlescent agent from Merck | 2% |

1 g of this composition was applied to a 2.7 g lock of brown hair that had previously been shampooed. The lock was dried with a hairdryer for 30 min. The lock was heated by being wound around a curling iron at 200° C. to obtain a "ringlet" with bluish highlights. The lock was shiny and soft.

Example 3

| | |
|---|---|
| POLYUREADIMETHICONE (WACKER-BELSIL UD 80) | 10% |
| CYCLOPENTASILOXANE DOW CORNING 245 FLUID | 35% |
| ETHANOL | 55% |

1 g of this composition was applied to a 2.7 g lock of brown hair that had previously been shampooed. The lock was dried with a hairdryer at a temperature below 50° C. for 30 min. The lock was heated and structured with a waving iron at 200° C. and waves were obtained over the entire surface of the lock. It was then shampooed. The deposit was still present on the hair and made it possible to reapply the waving iron to obtain the same effect of waves in the hair as previously achieved, thus demonstrating a durable effect.

Example 4

| | |
|---|---|
| POLYUREADIMETHICONE (WACKER-BELSIL UD 80) | 5% |
| ISODODECANE | 40% |
| ETHANOL | 55% |

1 g of this composition was applied to a 2.7 g lock of brown hair that had previously been shampooed. The lock was dried with a hairdryer at a temperature below 50° C. for 30 min. The lock was heated and structured with a waving iron at 200° C. and waves were obtained over the entire surface of the lock. It was then shampooed. The deposit was still present on the hair and made it possible to reapply the waving iron to obtain the same effect of waves in the hair as previously achieved, thus demonstrating durable effect.

Example 5

| | |
|---|---|
| POLYUREADIMETHICONE (WACKER-BELSIL UD 80) | 5% |
| ISODODECANE | 30% |
| ETHANOL | 55% |
| Prestige Soft pearlescent agent from Eckart | 10% |

1 g of this composition was applied to a 2.7 g lock of brown hair that had previously been shampooed. The lock was dried with a hairdryer at a temperature below 50° C. for 30 min. The lock was heated and structured with a waving iron at 200° C. and waves were obtained over the entire surface of the lock, and also a bronze-colored highlight. It was then shampooed. The deposit was still present on the hair and made it possible to reapply the waving iron to obtain the same effect of waves in the hair as previously achieved, and the color was also still present, thus demonstrating a durable effect.

What is claimed is:

1. A process for treating hair fibers comprising:
applying to the hair fibers at least one cosmetic composition comprising, in a cosmetically acceptable medium, at least one non-ionic polysiloxane/polyurea block copolymer, and
heating the hair fibers at a temperature ranging from 60 to 280° C.,
wherein the heating step occurs either simultaneously with, or successively to, the applying step;
wherein the at least one copolymer comprises only polysiloxane blocks and polyurea blocks; and
wherein the polysiloxane block of the at least one copolymer is present in an amount greater than 50% by weight, relative to the total weight of the copolymer.

2. The process of claim 1, wherein the polysiloxane block of the at least one copolymer is present in an amount greater than 90% by weight, relative to the total weight of the copolymer.

3. The process of claim 1, wherein the at least one polysiloxane/polyurea copolymer is chosen from those of formula (I):

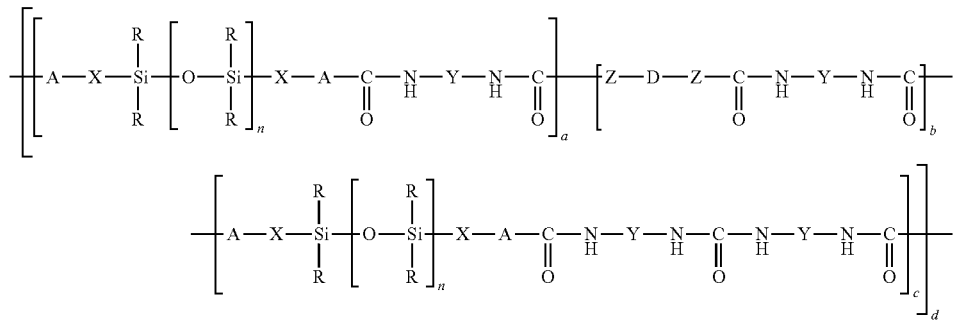

wherein:
R is a monovalent hydrocarbon-based radical, optionally substituted by fluorine or chlorine, having 1 to 20 carbon atoms;
X is an alkylene radical having 1 to 20 carbon atoms, in which non-neighboring methylene units may be replaced by —O— radicals;

A is an oxygen atom or an —NR'— amino radical;
Z is an oxygen atom or an —NR'— amino radical;
R' is hydrogen or an alkyl radical having 1 to 10 carbon atoms;
Y is a divalent hydrocarbon-based radical, where appropriate optionally substituted by fluorine or chlorine, having 1 to 20 carbon atoms;
D is an alkylene radical, optionally substituted by fluorine, chlorine, $C_1$-$C_6$ alkyl or $C_1$-$C_6$ alkyl ester, having 1 to 700 carbon atoms, wherein non-neighboring methylene units may be replaced by —O—, —COO—, —OCO— or —OCOO— radicals;
n is a number ranging from 1 to 4,000;
a is a number of at least 1;
b is a number ranging from 0 to 40;
c is a number ranging from 0 to 30; and
d is a number greater than 0,
on the condition that A is an —NH— radical in at least one of the (a) units.

4. A process of claim 1, wherein the at least one copolymer is obtained by a process comprising:
reacting a cyclic silazane of formulae (2) or (2'):

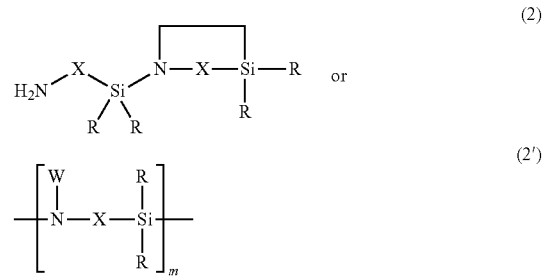

with an organic silicon compound of formula (3):

$$(HO)(R_2SiO)_{n-1}[H] \quad (3)$$

to give an aminoalkylpolydiorganosiloxane of formula (4):

$$H_2N-X-[SiR_2O]_nSiR_2-X-NH_2 \quad (4);$$

wherein the aminoalkylpolydiorganosiloxane of formula (4) is then polymerized with a diisocyanate of formula (5):

$$OCN-Y-NCO \quad (5); \text{ and}$$

further wherein

X is an alkylene radical having 1 to 20 carbon atoms, in which non-neighboring methylene units may be replaced by —O— radicals;

Y is a divalent hydrocarbon-based radical, where appropriate optionally substituted by fluorine or chlorine, having 1 to 20 carbon atoms;

R is a monovalent hydrocarbon-based radical, optionally substituted by fluorine or chlorine, having 1 to 20 carbon atoms; and n is a number ranging from 1 to 4,000.

5. A process of claim 1, wherein the at least one copolymer is polyureadimethicone.

6. A process of claim 1, wherein the at least one non-ionic polysiloxane/polyurea block copolymer is present in an amount ranging from 0.05 to 20%, relative to the weight of the composition.

7. A process of claim 1, wherein the at least one non-ionic polysiloxane/polyurea block copolymer is present in an amount ranging from 0.1 to 15% of the weight of the composition applied.

8. A process of claim 1, wherein the at least one non-ionic polysiloxane/polyurea block copolymer is present in an amount ranging from 0.5 to 10% of the weight of the composition applied.

9. A process of claim 1, wherein the at least one composition further comprises at least one adjuvant chosen from organomodified silicones; cationic, non-ionic, anionic and amphoteric polymers; peptides and derivatives thereof; protein hydrolysates; waxes; swelling agents; penetrants; anionic, cationic, non-ionic, amphoteric and zwitterionic surfactants; agents for combating hair loss; anti-dandruff agents; natural and synthetic associative and non-associative thickeners; suspension agents; sequestering agents; sunscreens; vitamins and provitamins; fatty acids; fatty alcohols; mineral, plant and synthetic oils; fragrances and preservatives.

10. A process of claim 1, wherein the at least one composition is applied to wet hair fibers.

11. A process of claim 1, wherein the hair fibers are heated at a temperature ranging from 120 to 220° C.

12. A process of claim 1, further comprising at least one additional operation chosen from permanent waving, oxidation dyeing, bleaching, and straightening.

* * * * *